United States Patent
Honjo et al.

(10) Patent No.: US 11,701,091 B2
(45) Date of Patent: Jul. 18, 2023

(54) ULTRASOUND ANALYSIS APPARATUS AND METHOD FOR TISSUE ELASTICITY AND VISCOSITY BASED ON THE HORMONIC SIGNALS

(71) Applicant: Canon Medical Systems Corporation, Otawara (JP)

(72) Inventors: Yasunori Honjo, Utsunomiya (JP); Masaki Watanabe, Utsunomiya (JP); Tetsuya Kawagishi, Nasushiobara (JP); Keita Yonemori, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 1000 days.

(21) Appl. No.: 16/282,509

(22) Filed: Feb. 22, 2019

(65) Prior Publication Data
US 2019/0261953 A1  Aug. 29, 2019

(30) Foreign Application Priority Data

Feb. 23, 2018 (JP) ................. 2018-030902
Feb. 20, 2019 (JP) ................. 2019-028443

(51) Int. Cl.
*A61B 8/08* (2006.01)
*A61B 8/15* (2006.01)
(Continued)

(52) U.S. Cl.
CPC ............ *A61B 8/5207* (2013.01); *A61B 8/085* (2013.01); *A61B 8/0841* (2013.01); *A61B 8/145* (2013.01);
(Continued)

(58) Field of Classification Search
CPC ..... A61B 8/485; A61B 8/5207; A61B 8/0841; A61B 8/085; A61B 8/145; A61B 8/15;
(Continued)

(56) References Cited

U.S. PATENT DOCUMENTS

2010/0069756 A1  3/2010  Ogasawara et al.
2011/0172538 A1  7/2011  Sumi
(Continued)

FOREIGN PATENT DOCUMENTS

JP  2002-369817  12/2002
JP  2010-051554  3/2010
(Continued)

OTHER PUBLICATIONS

Chen et al Shearwave Dispersion Ultrasound Vibrometry (SDUV) for Measuring Tissue Elasticity and Viscosity, IEEE Trans Ultrason Ferroelectr Freq Control. Jan. 2009 ; 56(1): 55-62.*
(Continued)

*Primary Examiner* — Serkan Akar
(74) *Attorney, Agent, or Firm* — Oblon, McClelland, Maier & Neustadt, L.L.P.

(57) ABSTRACT

According to one embodiment, an analysis apparatus includes processing circuitry. The processing circuitry configured to generate a harmonic signal and a fundamental wave signal based on a reception signal that is collected by an ultrasound probe, the harmonic signal corresponding to a harmonic component of a reflected wave of a ultrasound generated in the subject, the fundamental wave signal corresponding to a fundamental wave component of the reflected wave, calculate a first index value indicating tissue properties of the subject based on the harmonic signal, and calculate a second index value indicating the tissue properties based on the fundamental wave signal, and display an analysis result based on the first index value and the second index value.

11 Claims, 11 Drawing Sheets

(51) Int. Cl.
| | |
|---|---|
| *A61B 8/00* | (2006.01) |
| *G01S 15/89* | (2006.01) |
| *A61B 8/14* | (2006.01) |
| *A61B 17/34* | (2006.01) |
| *G06T 7/11* | (2017.01) |
| *G06T 7/00* | (2017.01) |
| *G01S 7/52* | (2006.01) |
| *A61B 17/00* | (2006.01) |
| *A61B 90/00* | (2016.01) |
| *A61B 5/15* | (2006.01) |

(52) U.S. Cl.
CPC .............. *A61B 8/15* (2013.01); *A61B 8/4477* (2013.01); *A61B 8/4494* (2013.01); *A61B 8/461* (2013.01); *A61B 8/463* (2013.01); *A61B 8/466* (2013.01); *A61B 8/481* (2013.01); *A61B 8/483* (2013.01); *A61B 8/485* (2013.01); *A61B 8/5223* (2013.01); *A61B 8/5246* (2013.01); *G01S 7/52022* (2013.01); *G01S 7/52038* (2013.01); *G01S 7/52042* (2013.01); *G01S 7/52071* (2013.01); *G01S 7/52074* (2013.01); *G01S 7/52077* (2013.01); *G01S 7/52085* (2013.01); *G01S 15/8915* (2013.01); *G06T 7/0012* (2013.01); *G06T 7/11* (2017.01); *G06T 7/97* (2017.01); *A61B 5/150748* (2013.01); *A61B 8/0891* (2013.01); *A61B 8/469* (2013.01); *A61B 2017/00106* (2013.01); *A61B 2017/3413* (2013.01); *A61B 2090/378* (2016.02); *G06T 2207/10132* (2013.01); *G06T 2207/20224* (2013.01)

(58) Field of Classification Search
CPC ..... A61B 8/4477; A61B 8/4494; A61B 8/461; A61B 8/463; A61B 8/466; A61B 8/481; A61B 8/483; A61B 8/5223; A61B 8/5246; A61B 5/150748; A61B 8/0891; A61B 8/469; A61B 2017/00106; A61B 2017/3413; A61B 2090/378; G01S 7/52022; G01S 7/52038; G01S 7/52042; G01S 7/52071; G01S 7/52074; G01S 7/52077; G01S 7/52085; G01S 15/8915; G06T 7/0012; G06T 7/11; G06T 7/97; G06T 2207/10132; G06T 2207/20224; G16H 50/30

See application file for complete search history.

(56) References Cited

U.S. PATENT DOCUMENTS

| | | |
|---|---|---|
| 2014/0276049 A1 | 9/2014 | Doherty et al. |
| 2015/0164480 A1* | 6/2015 | Watanabe ............ A61B 8/5246 600/440 |
| 2016/0120514 A1 | 5/2016 | Aragaki |
| 2016/0157828 A1 | 6/2016 | Sumi et al. |
| 2016/0262729 A1 | 9/2016 | Srinivasan et al. |

FOREIGN PATENT DOCUMENTS

| | | |
|---|---|---|
| JP | 2010-068904 | 4/2010 |
| JP | 2015-042344 | 3/2015 |
| JP | 2016-086947 | 5/2016 |

OTHER PUBLICATIONS

Extended European Search Report dated Sep. 17, 2019 in corresponding European Patent Application No. 19158854.0, 15 pages.
Atul N. Ingle et al., "Ultrasonic Tracking of Shear Waves Using a Particle Filter", Medical Physics, XP012201747, vol. 42, No. 11, Nov. 2015, pp. 6711-6724.
Partial European Search Report dated Jul. 15, 2019 in corresponding European Patent Application No. 19158854.0, 14 pages.
Michel Claudon et al. "Advances in Ultrasound", European Radiol., Ultrasound, vol. 12, No. 1, XP009071167, Jun. 1, 2005, pp. 7-18.
Office Action dated Jan. 31, 2023 in Japanese Application No. 2019-028443.

* cited by examiner

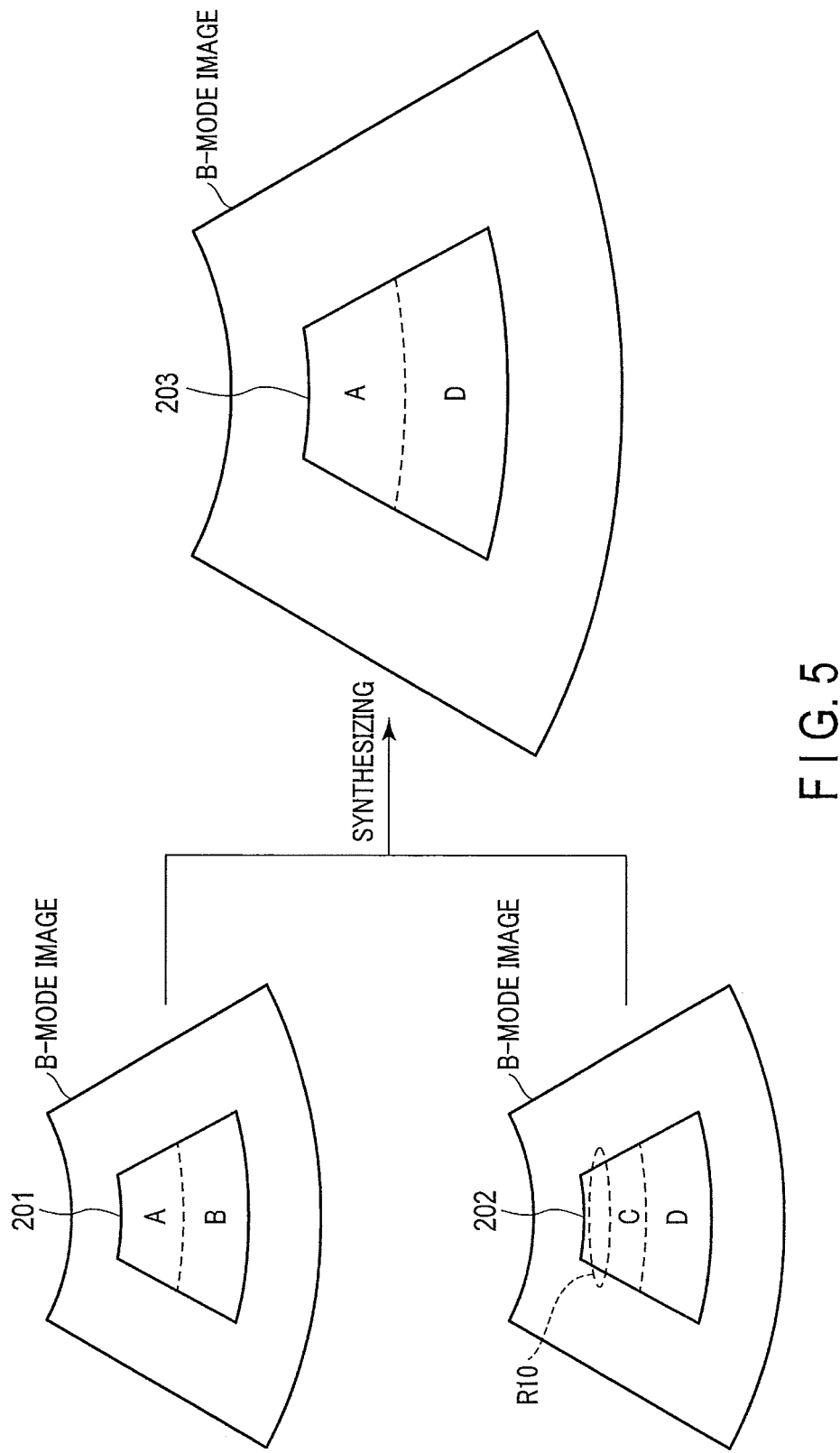
F I G. 5

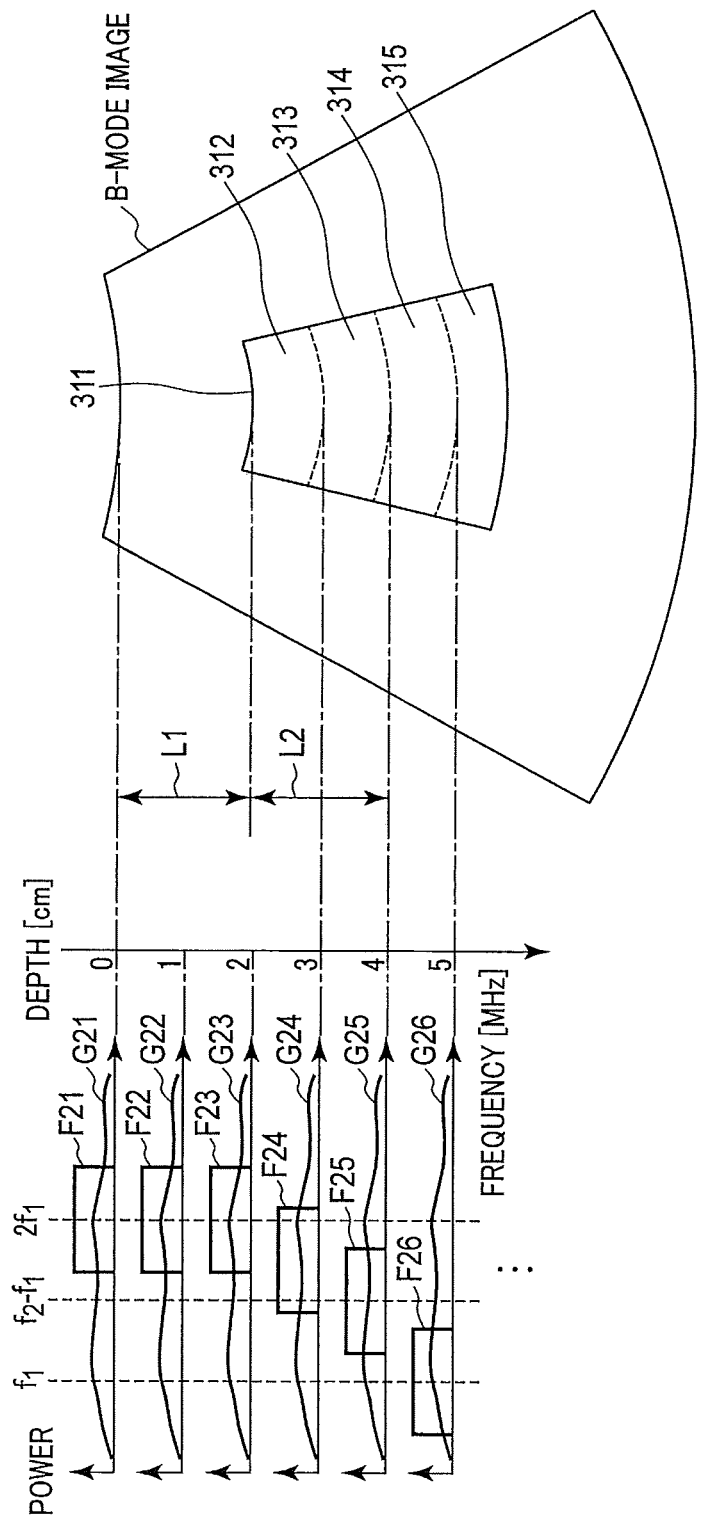
F I G. 13

ULTRASOUND ANALYSIS APPARATUS AND METHOD FOR TISSUE ELASTICITY AND VISCOSITY BASED ON THE HORMONIC SIGNALS

CROSS-REFERENCE TO RELATED APPLICATIONS

This application is based upon and claims the benefit of priority from Japanese Patent Applications No. 2018-030902, filed Feb. 23, 2018; and No. 2019-028443, filed Feb. 20, 2019; the entire contents of both of which are incorporated herein by reference.

FIELD

Embodiments described herein relate generally to an analysis apparatus and an analysis method.

BACKGROUND

In recent years, attempts have been made to quantify properties of living tissue, etc., with the use of an analysis apparatus, such as a medical diagnosis apparatus and a workstation. For example, an ultrasound diagnosis apparatus obtains index values related to elasticity and viscosity of living tissue by analyzing results of transmission and reception of ultrasound to the living tissue (ultrasound scanning). A function of quantifying the elasticity of living tissue and displaying the quantified elasticity to an operator in the form of images or numerical values may be called "electrography."

A result of ultrasound scanning may include noise due to "multiple reflections". "Multiple reflections" is a phenomenon in which an ultrasonic wave transmitted from an ultrasound probe is repeatedly reflected within a region proximate to a body surface. Since the aforementioned index values are obtained based on results of ultrasound scanning, the values are susceptible to multiple reflections.

BRIEF DESCRIPTION OF THE DRAWINGS

FIG. 5 is a diagram illustrating a synthesized elasticity image that the ultrasound diagnosis apparatus according to the embodiment displays on a display device.

FIG. 13 is a diagram illustrating a process of displaying a synthesized elasticity image by the ultrasound diagnosis apparatus according to the another embodiment.

DETAILED DESCRIPTION

In general, according to one embodiment, an analysis apparatus includes processing circuitry. The processing circuitry configured to generate a harmonic signal based on a reception signal that is collected by an ultrasound probe, and generate a fundamental wave signal based on the reception signal, the ultrasound probe transmitting ultrasound to a subject, receiving a reflected wave of the ultrasound generated in the subject, and generating the reception signal based on the reflected wave, the harmonic signal corresponding to a harmonic component of the reflected wave, the fundamental wave signal corresponding to a fundamental wave component of the reflected wave, calculate a first index value indicating tissue properties of the subject based on the harmonic signal, and calculate a second index value indicating the tissue properties based on the fundamental wave signal, and display an analysis result based on the first index value and the second index value.

Embodiments will be described below with reference to the drawings.

Embodiment

An ultrasound diagnosis apparatus 1 according to the present embodiment will be described with reference to the block diagram of FIG. 1. The ultrasound diagnosis apparatus 1 according to the present embodiment is, for example, an apparatus capable of performing elastography. Elastography is a technique of visualizing the distribution of the stiffness of living tissue based on measurements of said stiffness of living tissue. For example, the ultrasound diagnosis apparatus 1, according to the present embodiment, performs elastography by applying acoustic radiation force to living tissue to cause displacement therein.

Figure 1:
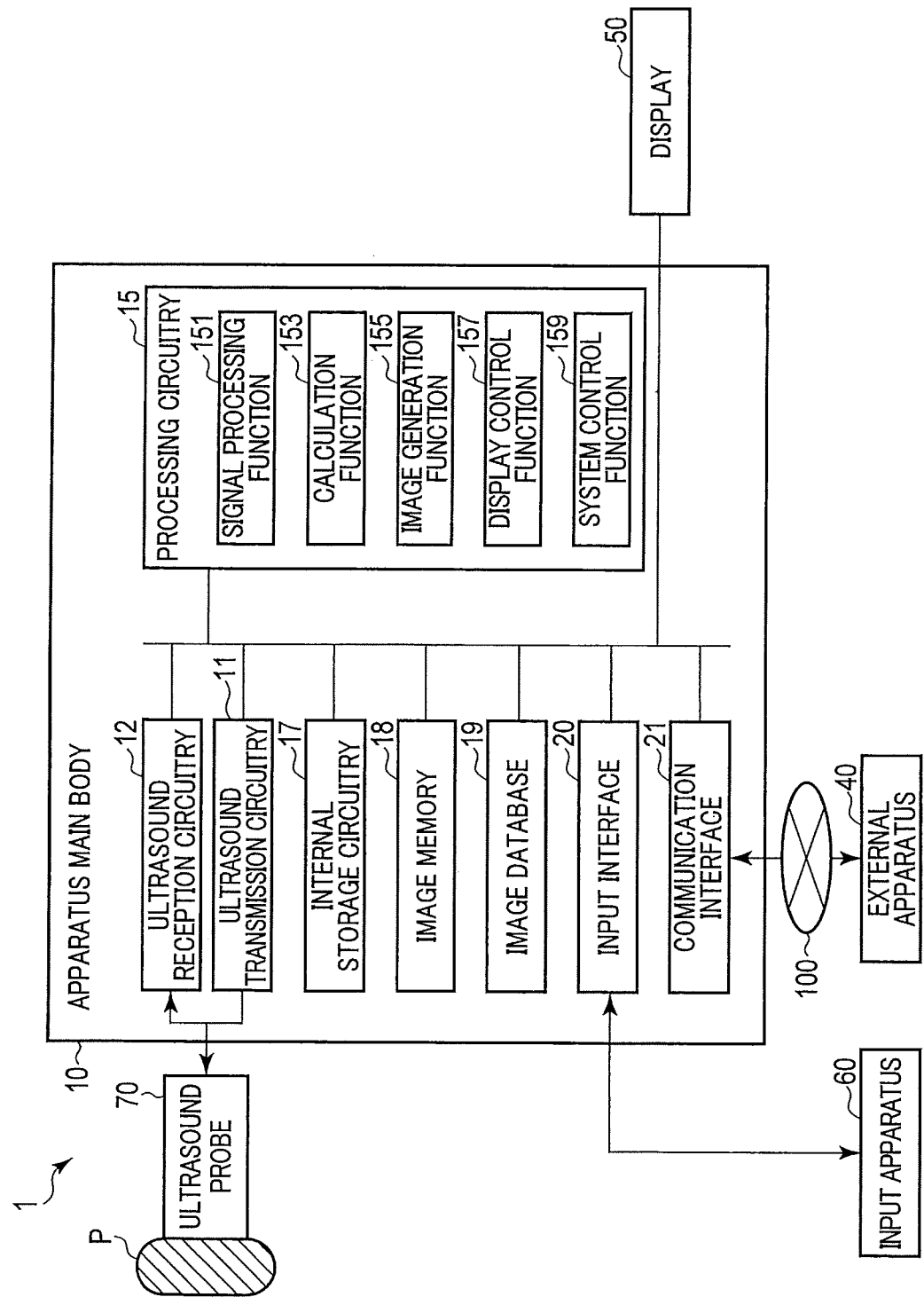
FIG. 1 is a diagram showing a configuration of an ultrasound diagnosis apparatus according to an embodiment.

As shown in FIG. 1, the ultrasound diagnosis apparatus 1 includes an apparatus main body 10, an ultrasound probe 70, a display 50, and an input device 60. The apparatus main body 10 is connected to an external apparatus 40 via a network 100. The apparatus main body 10 is connected to the display 50 and the input device 60.

The ultrasound probe 70 has a plurality of piezoelectric oscillators, a matching layer, and a backing member. The matching layer is provided in the piezoelectric oscillators. The backing member prevents backward propagation of ultrasound generated by the piezoelectric oscillators. The ultrasound probe 70 is detachably attached to the apparatus main body 10. The piezoelectric oscillators generate ultrasound based on a drive signal supplied from ultrasound transmission circuitry 11 included in the apparatus main body 10. The ultrasound probe 70 may be provided with buttons that are to be pressed for ultrasound image freezing.

When ultrasound is transmitted from the ultrasound probe 70 to a subject P, the transmitted ultrasound is reflected at an interface of media having different acoustic impedances in body tissue of the subject P, and the reflected wave (echo) is received at the piezoelectric oscillators of the ultrasound probe 70. An amplitude of a reception signal generated by the received reflected wave depends on a difference in acoustic impedances of the interface where ultrasound is reflected. In a case where the transmitted ultrasound pulse is reflected by a moving object, such as flowing blood or a surface like a cardiac wall, a reception signal is subjected to a frequency shift due to the Doppler effect, while depending on a velocity component of the moving object with respect to the direction of the transmitted ultrasound. The ultrasound probe 70 receives the reflected wave from the subject P, and converts it into an electrical signal (reception signal). A reception signal is thereby generated. The reception signal may be reworded as a reflected wave signal. The ultrasound probe 70 is, for example, a one-dimensional array probe in which piezoelectric oscillators are arranged in a predetermined direction, a two-dimensional array probe in which piezoelectric oscillators are arranged in a matrix, or a mechanical four-dimensional probe capable of performing ultrasound scanning while mechanically flapping a piezoelectric oscillator line in directions orthogonal to the alignment direction.

The apparatus main body 10 shown in FIG. 1 is an apparatus that generates an ultrasound image based on the reception signals received by the ultrasound probe 70. As shown in FIG. 1, the apparatus main body 10 includes ultrasound transmission circuitry 11, ultrasound reception circuitry 12, processing circuitry 15, internal storage circuitry 17, an image memory 18, an image database 19, an input interface 20, and a communication interface 21.

The ultrasound transmission circuitry 11 is a processor that supplies a drive signal to the ultrasound probe 70. The ultrasound transmission circuitry 11 is implemented by, for example, a trigger generation circuit, a delay circuit, and a pulse circuit. The trigger generation circuit repeatedly generates a rate pulse for forming ultrasound to be transmitted at a predetermined rate frequency under control of the control circuitry 15. The delay circuit provides each rate pulse generated by the trigger generation circuit with a delay time for each piezoelectric oscillator, which is necessary for converging ultrasound generated by the ultrasound probe 70 in a beam form and determining transmission directivity. The pulse circuit applies a drive signal (drive pulse) to the ultrasound probe 70 at times based on the rate pulse under the control of the processing circuitry 15. By varying the delay time provided to each rate pulse by the delay circuit, the transmission direction from the piezoelectric oscillator surface can be freely adjusted.

The ultrasound transmission circuitry 11, according to the present embodiment, causes the ultrasound probe 70 to transmit a push pulse to or around a region of interest (ROI) in a living body. This push pulse is a pulse having a long wave train length, compared to a normal ultrasound pulse, for example. Acoustic radiation force of the push pulse causes a shear wave in a living body, and propagation of this shear wave creates displacement at a location distant from the transmission location of the push pulse. The ultrasound transmission circuitry 11, according to the present embodiment, then causes the ultrasound probe 70 to transmit a tracking pulse multiple times to observe displacement caused by the push pulse in each sample point in the ROI. Each sample point represents a location in the ROI of the subject P, for example.

A shear wave caused by a single transmission of push pulse attenuates as the wave propagates. To observe the propagation of a shear wave across a large region, a shear wave caused by a push pulse transmitted at a specific location attenuates as the wave propagates, and when the wave is sufficiently distant from the transmission location of the push pulse, it becomes difficult to continue observing the propagation.

In such a case, it is necessary to transmit a push pulse at a plurality of locations in a lateral direction. For example, a region of interest is divided into multiple regions along the lateral direction. The ultrasound transmission circuitry 11 transmits a push pulse at different locations to cause shear waves, before transmitting and receiving a tracking pulse in each divided region. At this time, the transmission locations of the push pulse are typically set in the proximity of the divided regions. In a case where a parallel simultaneous reception number (the number of received beams generated at a single time of reception) is limited to a small number, the ultrasound transmission circuitry 11 performs, after transmitting a push pulse, the processing for transmission of a tracking pulse multiple times at each sample point in each of the divided regions along the lateral direction. For example, the ultrasound transmission circuitry 11 transmits and receives a tracking pulse after transmitting a push pulse in each of the divided regions.

The ultrasound reception circuitry 12 is a processor that performs various processes to the reception signal received by the ultrasound probe 70. The ultrasound reception circuitry 12 is realized by, for example, amplifier circuitry, an A/D converter, reception delay circuitry, and an adder. The amplifier circuitry performs a gain correction process by amplifying the reception signal received by the ultrasound probe 70 for each channel. The A/D converter converts the gain-corrected reception signal into a digital signal. The reception delay circuitry provides the digital signal with a delay time necessary for determining reception directivity. The adder sums a plurality of digital signals each provided with a delay time. By the summation process of the adder, a reception signal with an enhanced reflected component is generated in a direction corresponding to the reception directivity. The reception signal includes, for example, amplitude information reflecting the acoustic impedance difference between living tissue and living tissue of another type, and phase information reflecting movement of living tissue, such as a motion or travel speed, etc.

The ultrasound reception circuitry 12, according to the present embodiment, performs various processes to the reception signal corresponding to the tracking pulse transmitted by the ultrasound transmission circuitry 11 to the region of interest.

The processing circuitry 15 is a processor acting as a nerve center of the ultrasound diagnosis apparatus 1, for example. The processing circuitry 15 performs an operation program stored in the internal storage circuitry 17 to realize a function corresponding to the operation program. Specifically, the processing circuitry 15 includes a signal processing function 151 (signal processor), a calculation function 153 (calculator), an image generation function 155 (image generator), a display control function 157 (display controller), and a system control function 159.

The signal processing function 151 is a function to perform various kinds of signal processing on the reception signal generated by the ultrasound reception circuitry 12.

For example, by performing the signal processing function 151, the signal processing circuitry 15 performs an envelope wave detecting process, a logarithmic amplifying process, and the like, on the reception signal received from the ultrasound reception circuitry 12 to generate data that expresses signal intensity by brightness (B-mode data). The generated B-mode data is stored in a raw data memory (not shown) as B-mode raw data on an ultrasound scan line, which is two- or three-dimensionally distributed.

By performing the signal processing function 151, the processing circuitry 15 analyzes the reception signal received from the ultrasound reception circuitry 12 to calculate a moving speed of a moving object (blood or tissue) at each of the sample points in the region of interest, and generates Doppler data based on the calculated moving speed. The generated Doppler data is stored in a raw data memory (not shown) as Doppler raw data on an ultrasound scan line, which is two- or three-dimensionally distributed.

By performing the signal processing function 151 according to the present embodiment, the processing circuitry 15 generates frequency signal data of a frequency signal corresponding to a specific frequency component of the reflected wave based on the reception signal generated by the ultrasound reception circuitry 12. Specifically, the processing circuitry 15 generates, for example, a fundamental wave signal corresponding to a fundamental wave component of the reflected wave, or a harmonic signal corresponding to a harmonic component, by using a frequency filter. The frequency filter is, for example, a band-pass filter that extracts a certain frequency component, or a high-pass filter. At least one frequency filter is provided so as to pass a reception frequency according to a depth at which the reflected wave is generated. In other words, the processing circuitry 15 extracts a certain frequency component by filtering a reception signal with a frequency filter in accordance with a depth.

By performing the signal processing function 151, the processing circuitry 15 generates harmonic signal data based on a harmonic signal of the reflected wave by using a phase modulation (PM) method, an amplitude modulation (AM) method, or a combination of the PM method and the AM method. With the AM method, the PM method, or a combination of the AM and PM methods, ultrasound transmission is performed to a single sample point multiple times, with different amplitudes and/or phases. At this time, the processing circuitry 15 performs a summation process and/or a subtraction process to a plurality of reception signals at each sample point generated by the ultrasound reception circuitry 12, in accordance with a selected modulation method, thereby extracting a harmonic component. A case of using the PM method will be described below in detail.

For example, by performing the signal processing function 151, the processing circuitry 15 performs ultrasound transmission twice in a row in the same direction, in which the phases are different for 180 degrees from each other, and performs a summation or subtraction process to two reception signals generated as a result of the ultrasound transmissions, thereby extracting a fundamental wave component and an odd-order harmonic component, or only an even-order harmonic component. When the processing circuitry 15 performs a subtraction process to the two reception signals, a fundamental wave component with double the amplitude, and an odd-order harmonic component are extracted. When a summation process is performed to the two reception signals, an even-order harmonic component with double the amplitude is extracted. With respect to the extracted fundamental component and odd-order harmonic component, or the even-order harmonic component, the processing circuitry 15 generates a harmonic signal corresponding to the harmonic component of the reflected wave by further using a frequency filter, for example. The processing circuitry 15 may generate a fundamental wave signal corresponding to the fundamental wave component by further using a frequency filter with respect to the extracted fundamental wave component and odd-order fundamental component. In the phase modulation method, the number of times ultrasound is transmitted is not limited to two times. For example, ultrasound having a phase difference of 120 degrees may be transmitted three times, and the reception signals corresponding to the transmission of the three times may be synthesized to extract a third harmonic component. For example, a fundamental wave component is extracted from a reception signal corresponding to one of the three transmissions.

For another example, by performing the signal processing function 151, the processing circuitry 15 may simultaneously transmit ultrasound having multiple different central frequencies from the ultrasound probe 70, and may generate, for the reception signals generated as a result of the ultrasound transmission, a fundamental wave signal corresponding to a fundamental wave component, a difference tone signal corresponding to a difference tone component, and a harmonic signal corresponding to a harmonic component, by using a frequency filter. Alternatively, the processing circuitry 15 may generate a tone signal corresponding to a tone component.

The calculation function 153 is a function to calculate an index value indicating tissue properties in the subject P based on the fundamental wave signal and/or the harmonic signal, etc. generated by the signal processing function 151. By performing the calculation function 153, the processing circuitry 15 calculates the displacement that has been caused in the subject P by the use of phase information included in the fundamental wave signal and/or the harmonic signal, etc., generated by the signal processing function 151, and then calculates an index value indicating tissue properties in the subject P based on the calculated displacement. Specifically, the processing circuitry 15 analyzes the fundamental wave signal and/or the harmonic signal related to a tracking pulse, for example, and calculates an index value indicating tissue properties in each of the sample points in the region of interest. The index value indicating tissue properties is an index value that indicates, for example, elasticity or viscosity of tissue. The index value indicating elasticity of the tissue is, for example, a propagation speed of a shear wave caused by a push pulse. Hereinafter, a propagation speed of a shear wave will be referred to as a "shear wave speed". A shear wave speed is high in stiff tissue, and low in soft tissue. In other words, the larger a shear wave speed becomes, the larger a value indicating stiffness of tissue (modulus of elasticity) becomes.

Specifically, by performing the calculation function 153, the processing circuitry 15 calculates a moving speed of tissue at each sample point in the region of interest over multiple phases by using, for example, phase information of the fundamental signal related to a tracking pulse and/or phase information of the harmonic signal. Then, the processing circuitry 15 obtains time quadrature of the calculated moving speed of multiple phases. The processing circuitry 15 thereby calculates displacement at each sample point in the region of interest, for multiple phases. Subsequently, the processing circuitry 15 calculates a time when displacement becomes largest for each sample point. The processing circuitry 15 then obtains the time when the largest displacement occurs in each sample point as an arrival time of a shear wave at each sample point. Subsequently, the processing circuitry 15 calculates a shear wave speed at each sample point based on the arrival time of a shear wave at each sample point.

The processing circuitry 15, instead of calculating the shear wave speed based on the time when displacement becomes largest at each sample point, may calculate said shear wave speed based on a correlation between temporal changes of displacement created in two sample points aligned in the lateral direction, for example.

The processing circuitry 15 may calculate a Young's modulus or modulus of shear elasticity from the shear wave speed, defining the calculated Young's modulus (or a modulus of shear elasticity) as an index value indicating elasticity of tissue. Displacement, a shear wave speed, a Young's modulus, and a modulus of shear elasticity are physical quantities related to stiffness of living tissue. Displacement and a shear wave speed, etc. are also physical quantities related to motion of living tissue.

The processing circuitry 15 may calculate stiffness of a desired sample point (a local ROI) by using a Young's modulus.

The image generation circuitry 155 is a function capable of generating various ultrasound image data based on data generated by performing the signal processing function 151 or the calculation function 153. By performing the image generation function 155, the processing circuitry 15 generates B-mode image data based on the B-mode raw data stored in the raw data memory. A B-mode image based on the B-mode image data shows, for example, a form of a biological structure in the subject P. The B-mode image data has a pixel value (brightness value) reflecting, for example, characteristics of the ultrasound probe, such as sound convergence, and sound-field characteristics of an ultrasound beam (e.g., a transmitted/received beam). For example, B-mode image data has relatively higher brightness in the vicinity of the focus of ultrasound than in the unfocused part.

By performing the image generation function 155, the processing circuitry 15 generates Doppler image data representing information of a moving object based on the Doppler raw data stored in the raw data memory. The Doppler image data takes the form of speed image data, dispersion image data, power image data, or a combination thereof.

By performing the image generation function 155, the processing circuitry 15 generates tissue property image data representing a tissue property image of the region of interest, based on an index value indicating tissue properties calculated by the calculation function 153, for each sample point in the region of interest of the subject P. For example, the processing circuitry 15 generates elasticity image data in which the stiffness of living tissue is expressed by colors based on the shear wave speed calculated by the calculation function 153. For example, the processing circuitry 15 generates, as elasticity image data, shear wave speed image data in which a pixel value is allocated to each point of the ROI in accordance with a shear wave speed at that point. The elasticity image data is an example of tissue property image data.

The display control function 157 is a function of displaying an analysis result based on a first index value and a second index value. By performing the display control function 157, the processing circuitry 15, for example, causes the display 50 to display an elasticity image based on the elasticity image data generated by the image generation function 155.

The analysis result includes a synthesized tissue property image (a third tissue property image), for example. To display an analysis result includes at least one of the following: "to display a tissue property image (a third tissue property image) obtained by superimposing a first tissue property image with a second tissue property image", "to simultaneously display a third tissue property image and a difference image [to be described later]", "to simultaneously display a third tissue property image and a contour image [to be described later]", and "to simultaneously display a contour image and a difference image".

By performing the display control function 157, the processing circuitry 15 converts (scan-converts), in general, a scan line signal sequence of ultrasound scanning into, for example, a scan line signal sequence in a video format representatively used by television to generate ultrasound image data for display. Specifically, the image generation circuitry 15 performs a coordinate conversion in accordance with the form of ultrasound scanning by the ultrasound probe 70, to generate ultrasound image data for display.

By performing the display control function 157, the processing circuitry 15 may perform various processes, such as dynamic range, brightness, contrast, y curve corrections, and an RGB conversion, on generated various ultrasound image data. The processing circuitry 15 may add supplementary information, such as textual information of various parameters, a scale, or a body mark, to the generated various ultrasound image data.

By performing the display control function 157, the processing circuitry 15 may generate a user interface (graphical user interface: GUI) through which an operator (such as a person performing surgery), or the like, inputs various instructions by the input interface 20, and causes the display 50 to display the GUI. As the display 50, for example, a CRT display, a liquid crystal display, an organic EL display, an LED display, a plasma display, or any other display known in the relevant technical field may be used as appropriate.

An analysis result is not limited to images. An analysis result may be numerical information; stiffness value, for example. By performing the display control function 157, the processing circuitry 15 causes the display 50 to display a stiffness value calculated by the calculation function 153.

The system control function 159 is a function of controlling basic operations, such as the input and output and the transmission and reception of ultrasound, relative to the ultrasound diagnosis apparatus 1. By performing the system control function 159, the control circuitry 15 receives a start instruction to start various types of imaging modes, via the input interface 20. Various imaging modes include, for example, a B-mode, a Doppler mode, and an elastography mode. The elastography mode according to the present embodiment is a mode in which acoustic radiation force is applied to living tissue by the ultrasound probe on a body surface to cause displacement by a shear wave, and the displacement is observed with time in each point in a scanning cross section. For example, the control circuitry 15 receives the start instruction to start various types of imaging modes, via the input interface 20. And, for example, the processing circuitry 15 receives a start instruction to start, for example, an elastography mode via the input interface 20.

The signal processing function 151, the calculation function 153, the image generation function 155, the display controlling function 157, and the system control function 159 may be incorporated as control programs; otherwise, dedicated hardware circuits capable of performing respective functions may be incorporated in the processing circuitry 15 itself or the apparatus main body 10 as circuits that can be referred to by the processing circuitry 15.

The internal storage circuitry 17 includes, for example, a magnetic or optical storage medium, or a processor-readable storage medium such as a semiconductor memory. The internal storage circuitry 17 stores, for example, a control program for realizing ultrasound transmission and reception, a control program for performing image processing, and a control program for performing display processing. The internal storage circuitry 17 also stores a control program for realizing various functions according to the present embodiment. The internal storage circuitry 17 also stores diagnostic information (such as a patient's ID, and a doctor's observation), a diagnostic protocol, a body mark generation program, and a data group such as a conversion table in which the range of color data used for imaging is preset for each diagnostic site. The internal storage circuitry 17 may store anatomical illustrations, for example, an atlas, relating to the structures of internal organs in the body.

The internal storage circuitry 17 stores various ultrasound image data generated by the image generation function 155, in accordance with a storing operation that is input via the input interface 20. The internal storage circuitry 17 may store various ultrasound image data generated by performing the image generation function 155 together with the operation order and operation time, in accordance with a storing operation input via the input interface 20. The internal storage circuitry 17 can transfer the stored data to an external device via the communication interface 21.

The image memory 18 includes, for example, a magnetic or optical storage medium, or a processor-readable storage medium such as a semiconductor memory. The image memory 18 stores image data for display generated by performing the image generation function 155. The image memory 18 stores image data corresponding to a plurality of frames immediately before a freeze operation input via the input interface 20. The image data stored in the image memory 18 is, for example, continuously displayed (cine-displayed).

The image data stored in the image memory 18 is, for example, image data representing an image actually displayed on the display 50. This image may include an image based on ultrasound image obtained by an ultrasound scan, and an image based on diagnostic image data obtained by another modality, such as computed tomography (CT) image data, magnetic resonance (MR) image data, X-ray image data, or positron emission tomography (PET) image data.

The image memory 18 can also store data generated by performing the signal processing function 151. The B-mode data and Doppler data stored in the image memory 18 can be taken out by the operator, for example, after diagnosis, and turned into ultrasound image data for display through the processing circuitry 15.

The image database 19 stores image data transferred from the external device 40. For example, the image database 19 acquires, from the external device 40, past image data related to a particular patient acquired from past diagnosis, and stores the acquired image data. The historic image data includes ultrasound image data, CT image data, MR image data, PET-CT image data, PET-MR image data, and X-ray image data. The historic image data is stored as, for example, volume data and rendering image data.

The image database 19 may store a desired image data by reading image data stored in a storage medium such as an MO, a CD-R and a DVD.

The input interface 20 receives various types of instructions from an operator through the input device 60. The input device 60 includes, for example, a mouse, a keyboard, a panel switch, a slider switch, a dial switch, a track ball, a rotary encoder, an operation panel, and a touch command screen (TCS). The input device 60 includes a switch group for switching various imaging modes including an ultrasound transmission/reception scheme, and reception signal processing scheme, etc. The switch group may be not only a mechanical device, such as a dial switch or a track ball, but also an operation panel image displayed on a TCS, or an operation panel image displayed on a second console in the external apparatus 40.

The input interface 20, connected to the processing circuitry 15 via, for example, a bus, converts an operation instruction that is input by the operator into an electrical signal, and outputs the electrical signal to the processing circuitry 15. In the present embodiments, the input interface 20 is not limited to be connected to physical operation components such as a mouse, a keyboard, etc. An example of the input interface 20 includes processing circuitry which receives, as radio signals from the ultrasound diagnosis apparatus 1, electric signals corresponding to an operation instruction input from an external input device independently provided and outputs the electric signals to the processing circuitry 15.

The communication interface 21 is connected to the external apparatus 40 via, for example, the network 100, and performs data communication with the external apparatus 40. The external apparatus 40 is, for example, a database of a picture archiving and communication system (PACS) which is a system that manages data of various medical images, and a database of an electronic health record system which manages electronic health records accompanied with medical images. The external apparatus 40 is also, for example, various medical image diagnostic apparatuses other than the ultrasound diagnostic apparatus 1 according to the present embodiment, such as an X-ray CT apparatus, a magnetic resonance imaging (MRI) apparatus, nuclear medicine diagnostic apparatus, and an X-ray diagnostic apparatus. The standard of the communication with the external apparatus 40 may be set at any standard, but is, for example, DICOM.

Figure 2:
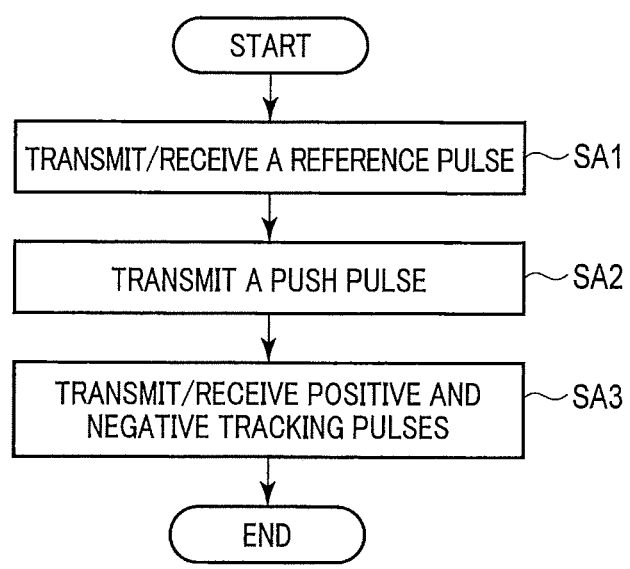
FIG. 2 is a flowchart of ultrasound scanning performed by the ultrasound diagnosis apparatus according to the embodiment.

Next, operations of the ultrasound diagnosis apparatus 1 according to the present embodiment will be described with reference to the drawings. First, the flow of the ultrasound scanning performed by the ultrasound diagnosis apparatus 1 according to the present embodiment will be described with reference to FIG. 2. FIG. 2 is a flowchart of the ultrasound scanning performed by the ultrasound diagnosis apparatus 1 according to the present embodiment. The operations shown in the flowchart are implemented by, for example, the system control function 159. In the following description, let us suppose that a start instruction to start the elastography mode is input via the input interface 20. Let us further suppose that the processing circuitry 15 performs the PM method or filtering to generate a harmonic signal of the reflected wave.

As shown in FIG. 2, the processing circuitry 15 performs the system control function 159, and receives a start instruction to start the elastography mode via the input interface 20. Upon reception of the start instruction, the processing circuitry 15 controls the ultrasound transmission circuitry 11 to transmit a reference pulse to a specific divided region (hereinafter a region of interest) of a subject P (step SA1). The processing circuitry 15 then controls the ultrasound reception circuitry 12 to perform various processes to the reception signal received by the ultrasound probe 70, corresponding to the transmitted reference pulse, and generates a reception signal corresponding to the reference pulse. The reference pulse is a pulse transmitted to calculate a criterion of displacement at each sample point in the subject P.

Next, the processing circuitry 15 controls the ultrasound transmission circuitry 11 to transmit a push pulse to the region of interest (step SA2). For example, the processing circuitry 15 transmits a push pulse from a specific transmission location to cause a shear wave, before a tracking pulse is transmitted and received in the region of interest. At this time, the transmission location of the push pulse is typically set in the proximity of the region of interest.

Subsequently, the processing circuitry 15 controls the ultrasound transmission circuitry 11, and transmits a tracking pulse multiple times to each sample point along the lateral direction in the region of interest (step SA3). At this time, the processing circuitry 15 transmits, at least once, a positive tracking pulse and a negative tracking pulse, which has a phase different from that of the positive tracking pulse for 180 degrees, at each sample point in the region of interest. The processing circuitry 15 controls the ultrasound reception circuitry 12, and performs various processes to a reception signal corresponding to the transmitted positive tracking pulse. The processing circuitry 15 also performs various processes to a reception signal corresponding to the transmitted negative tracking pulse. The 180-degree phase difference may be reworded as "phase-inverted".

The processing circuitry 15 performs the process in step SA1 through step SA3 in each of the divided regions.

Figure 3:
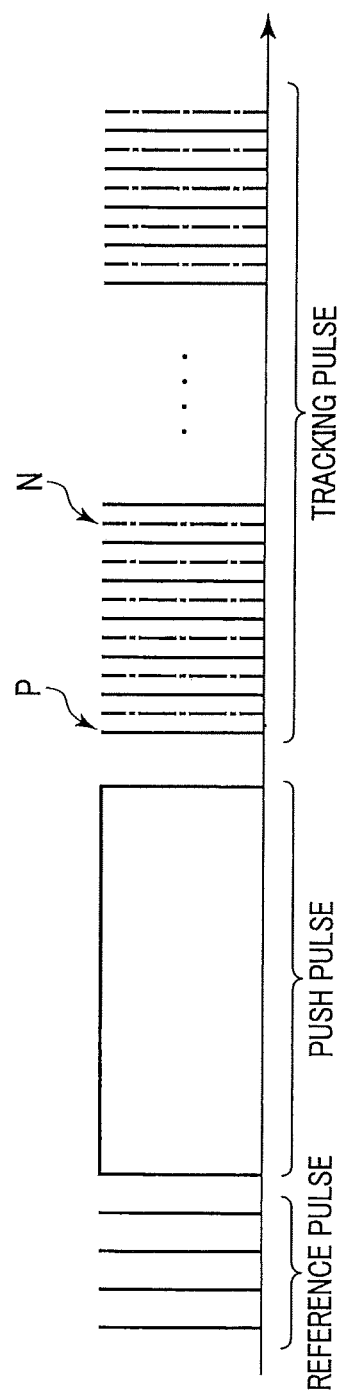
FIG. 3 is a diagram illustrating a flow of the ultrasound scanning performed by the ultrasound diagnosis apparatus according to the embodiment.

FIG. 3 is a diagram illustrating a flow of ultrasound scanning performed by the ultrasound diagnosis apparatus 1 according to the present embodiment. As shown in FIG. 3, the processing circuitry 15 controls the ultrasound transmission circuitry 11, and transmits ultrasound pulses, specifically a reference pulse, a push pulse, and a tracking pulse in this order. As shown in FIG. 3, the processing circuitry 15 transmits, at least once, a positive tracking pulse P and a negative tracking pulse N to each sample point in the region of interest. A scanning sequence like the one shown in FIG. 3 is repeated for each divided region, for example.

In the present embodiment, positive and negative tracking pulses are transmitted in the scanning sequence; however, positive and negative reference pulses may also be transmitted.

Figure 4:
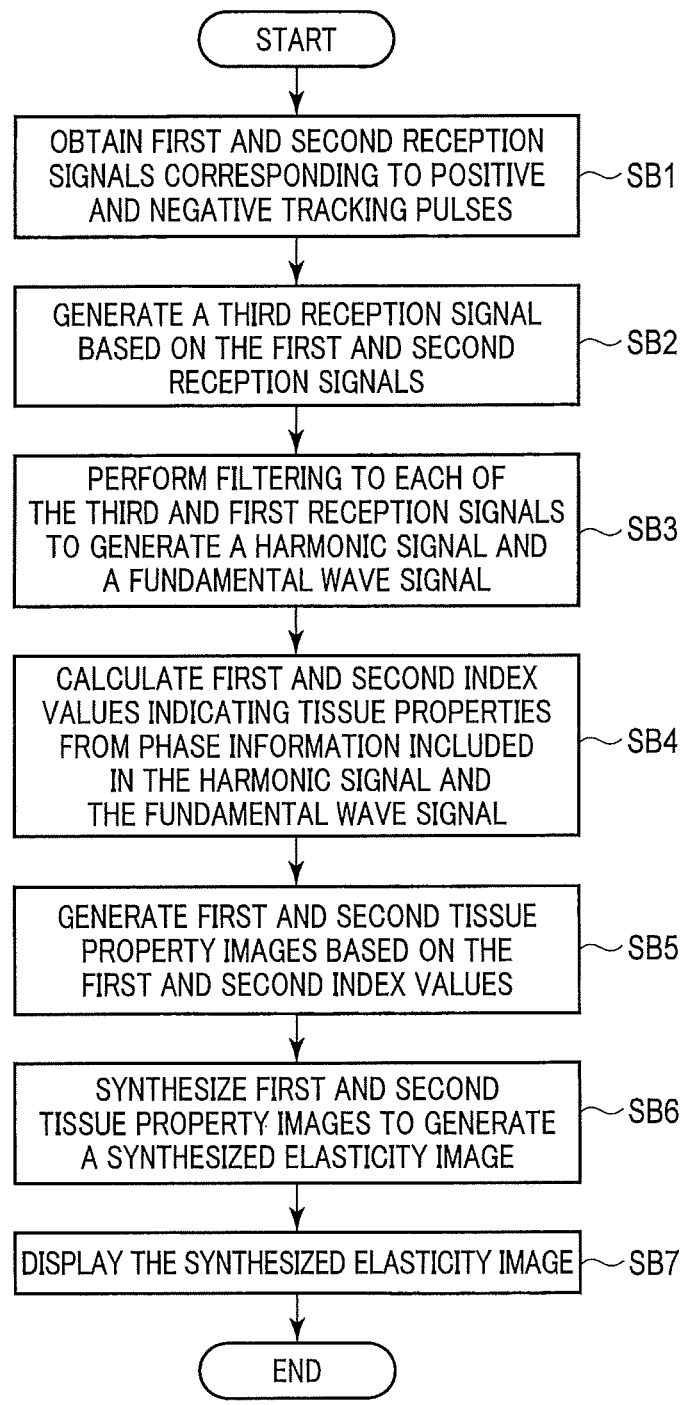
FIG. 4 is a flowchart of operations of processing circuitry when the ultrasound diagnosis apparatus according to the embodiment displays a synthesized elasticity image.

Next, with reference to FIG. 4, an operation of the processing circuitry 15 when the ultrasound diagnosis apparatus 1 according to the present embodiment displays a synthesized elasticity image. FIG. 4 is a flowchart of operations of the processing circuitry 15 when the ultrasound diagnosis apparatus 1 according to the embodiment displays a synthesized elasticity image. The operations shown in the flowchart are implemented by the signal processing function 151, the calculation function 153, and the image generation function 155. In the following description, let us suppose that the process in step SB1 (shown in FIG. 4) is started after the performance of the process in step SA1 through step SA3 (shown in FIG. 2) in all the divided regions. The process in step SA1 through step SA3 (shown in FIG. 2), and the process in step SB1 through step SB4 (shown in FIG. 4) may be performed for each divided region.

The processing circuitry 15 performs the signal processing function 151, and obtains a reception signal of the positive tracking pulse (a first reception signal) and a reception signal of the negative tracking pulse (a second reception signal) for all the divided regions (step SB1). A phase difference between the first reception signal and the second reception signal is, for example, 180 degrees. At this time, the processing circuitry 15 obtains the reception signal of a reference pulse generated at step SA1 shown in FIG. 2.

The processing circuitry 15 generates a reception signal from which a fundamental wave component is removed (a third reception signal) based on the first and second reception signals obtained in step SB1 (step SB2). For example, the processing circuitry 15 generates a third reception signal for which an even-order harmonic component, for example a second harmonic component, by performing a summation process to the first and second reception signals.

The processing circuitry 15 performs filtering on the generated third reception signal, using a filter for extracting only a second harmonic component (a first frequency filter). The processing circuitry 15 performs filtering on the first reception signal, using a filter for extracting only a fundamental wave component (a second frequency filter). By those processes, a harmonic signal corresponding to a second harmonic component and a fundamental wave signal corresponding to the fundamental wave component are generated (step SB3). The filtering in step SB3 can be omitted, if a harmonic component included in each reception signal is low enough to be ignored.

The fundamental wave signal corresponding to a fundamental wave component may be generated as described below. The processing circuitry 15 takes a difference between the first reception signal and the second reception signal so as to generate a reception signal from which an even-order harmonic component is removed. The processing circuitry 15 performs filtering on the generated reception signal using the second frequency filter, so as to generate a fundamental wave signal corresponding to a fundamental wave component.

The processing circuitry 15 performs the calculation function 153 to calculate an index value indicating tissue properties, for example shear wave speed (a first index value) at each sample point, using phase information included in the harmonic signal generated in step SB3. The processing circuitry 15 calculates an index value indicating tissue properties, for example a shear wave speed (a second index value) at each sample point, using phase information included in the fundamental wave signal generated in step SB3 (step SB4).

Specifically, first, the processing circuitry 15 calculates displacement caused at each sample point in the subject P, which is used as a criterion, by using the reception signal corresponding to the reference pulse obtained in step SB1. Subsequently, using the displacement calculated for the reception signal corresponding to the reference pulse as a criterion, the processing circuitry 15 calculates displacement at each sample point caused in the subject P by using phase information included in the harmonic signal. The processing circuitry 15 then calculates a shear wave speed (a first index value) at each sample point based on the calculated displacement at each sample point.

Using the displacement calculated for the reception signal corresponding to the reference pulse, the processing circuitry 15 calculates displacement caused at each sample point in the subject P by using the phase information included in the fundamental wave signal. The processing circuitry 15 calculates a shear wave speed (a second index value) at each sample point based on the displacement calculated for each sample point.

By performing the image generation function 155, the processing circuitry 15 generates, based on the first index value calculated in step SB4, elasticity image data representing an elasticity image based on a harmonic signal (a first tissue property image). The processing circuitry 15 generates elasticity image data representing an elasticity image based on a fundamental wave signal (a second tissue property image) based on the second index value generated in step SB4 (step SB5). Specifically, for example, the processing circuitry 15 performs color coding on the shear wave speed calculated for a harmonic signal, and maps the color-coded speed on a corresponding map point, thereby generating elasticity image data representing an elasticity image based on the harmonic signal. The processing circuitry 15 performs color coding on the shear wave speed calculated for a fundamental wave signal, and maps the color-coded speed on a corresponding map point, thereby generating elasticity image data representing an elasticity image based on the fundamental wave signal.

The processing circuit 15 synthesizes the elasticity image data based on the harmonic signal with the elasticity image based on the fundamental wave signal to generate a synthesized elasticity image (step SB6). The processing circuitry 15 generates synthesized elasticity image data by replacing a region susceptible to multiple reflections (hereinafter, a "multiplex region") in the elasticity image based on the fundamental wave signal with a region included in the elasticity image based on the harmonic signal and corresponding to the multiplex region.

The control circuitry 15 performs the display controlling function 157 to cause the display 50 to display a synthesized elasticity image based on the generated synthesized elasticity image data (step SB7). FIG. 5 is a diagram illustrating a synthesized elasticity image based on the synthesized elasticity image data that the ultrasound diagnosis apparatus 1 according to the present embodiment displays on the display 50. FIG. 5 illustrates a case where an elasticity image is superimposed on a location corresponding to a B-mode image in the elastography mode. According to FIG. 5, the processing circuitry 15 synthesizes the elasticity image data representing an elasticity image 201, based on a harmonic signal, with elasticity image data representing an elasticity image 202, based on a fundamental wave signal, to generate a synthesized elasticity image representing a synthesized elasticity image 203. A method of image synthesis will be specifically described below.

In FIG. 5, the multiplex region is not included in the elasticity image 201. In the elasticity image 202 on the other hand, noise due to multiple reflections is included in the region R10. The region R10 corresponds to the multiplex region. In the region R10, an estimated shear wave speed normally tends to be of a high value due to the influence of multiple reflections. This high value appears as noise on the elasticity image where pixel values are allocated to each point in accordance with a shear wave speed. For this reason, the processing circuitry 15 synthesizes, among a region C (which includes the region R10) and a region D (which does not include the region R10) in the elasticity image 202, the region D with, among a region A and a region B in the elasticity image 201, the region A corresponding to the region C. Synthesized elasticity image data representing the synthesized elasticity image 203 in which the influence of multiple reflections is reduced is thereby generated. The region A and the region C correspond to a first region, and the region B and the region D correspond to a second region.

The processing circuitry 15 may cause the display 50 to display the elasticity image based on the harmonic signal, and the elasticity image based on the fundamental wave signal, with the images being superimposed. In this case, the processing circuitry 15 generates superimposed image data representing a superimposed image by following Equation (1) below:

$$v_{swe} = \alpha \times v_{fund} + (1-\alpha) \times v_{thi} \quad (1)$$

Herein, $v_{swe}$ represents a pixel value based on a propagation speed in the superimposed image. $v_{fund}$ represents a pixel value based on a propagation speed in the elasticity image based on a fundamental wave signal. $v_{thi}$ represents a pixel value based on a propagation speed in the elasticity image based on a harmonic signal. $\alpha$ is a parameter controllable by the processing circuitry 15. For example, if $\alpha=0.5$ in Equation (1), image data representing an image consisting of the average values of the pixel values in the elasticity image based on the harmonic signal and in the elasticity image based on the fundamental wave signal, is generated.

The processing circuitry 15 may perform differential processing to the elasticity image data based on the harmonic signal and the elasticity image data based on the fundamental wave signal to extract a region susceptible to multiple reflections as a difference image, and thereby generate difference image data representing the difference image. The differential processing is expressed as the following equation (2):

$$v_{swe} = v_{fund} - v_{thi} (\text{if } v_{swe} \geq v_{thresh}), 0 (\text{if } v_{swe} < v_{thresh}) \quad (2)$$

Herein, $v_{thresh}$ is a threshold value predetermined for a difference between pixel values of the elasticity image based on the harmonic signal and pixel values of the elasticity image based on the fundamental wave signal, that is, a difference in propagation speed. The processing circuitry 15 may change $v_{thresh}$ to any value as appropriate. In general, in regions other than a region susceptible to multiple reflections, there are no differences in pixel values between the elasticity image based on the harmonic signal and the elasticity image based on the fundamental wave signal. In contrast, in a region susceptible to multiple reflections, larger pixel values tend to appear, compared to a case where multiple reflections do not occur in this region. It is thus possible to specify a region susceptible to multiple reflections by extracting a region having a pixel value equal to or greater than a threshold value, $v_{thresh}$.

Figure 6:
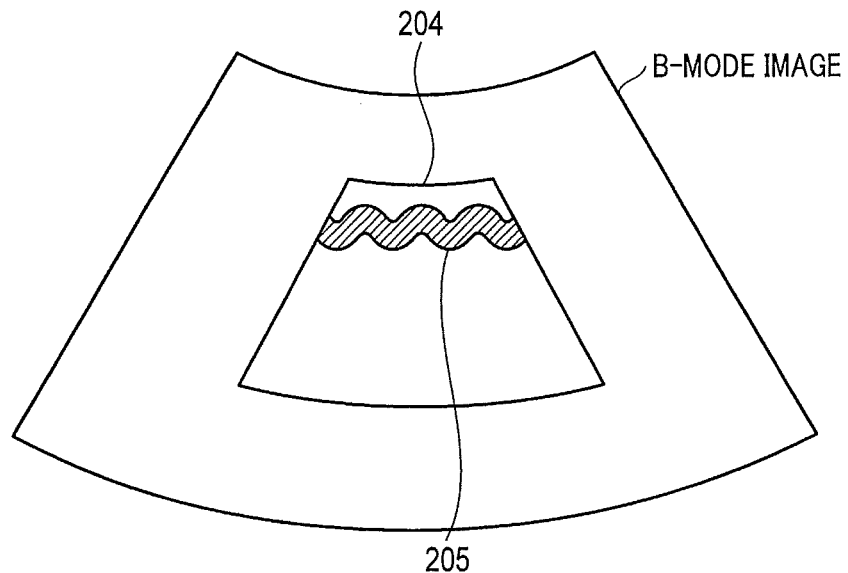
FIG. 6 is a schematic diagram showing a difference image that the ultrasound diagnosis apparatus according to the embodiment displays on a display device.

The processing circuitry 15 causes the display 50 to display the difference image based on the generated difference image data. FIG. 6 is a diagram showing an example of a schematic drawing of the difference image displayed on the display 50 by the ultrasound diagnosis apparatus 1 according to the present embodiment. FIG. 6 illustrates a case where a difference image is superimposed on a corresponding location on a B-mode image in the elastography mode. The difference image 204 is an image in which differences between the pixel values of the elasticity image based on the fundamental wave signal and those of the elasticity image based on the harmonic signal are emphasized, if the differences are equal to or greater than the threshold value $v_{thresh}$. In the difference image 204, the region 205 (indicated by shading) illustrates a group of pixels having values equal to or greater than the threshold value $v_{thresh}$. In the region 205 (indicated by shading), for each pixel included in the region, a pixel value, which is calculated by subtracting a pixel value of a pixel corresponding to the elasticity image based on the harmonic signal from a pixel value of a pixel of the elasticity image based on the fundamental wave signal, is allocated.

The processing circuitry 15 may cause the display 50 to display the elasticity image based on the harmonic signal and the elasticity image based on the fundamental wave signal, side by side. The processing circuitry 15 may cause the display 50 to display solely the elasticity image based on the harmonic signal. The processing circuitry 15 may cause the display 50 to display the difference image and the synthesized image simultaneously. The processing circuitry 15 displays the difference image and the synthesized image, side by side or via superimposition.

According to the present embodiment, the processing circuitry 15 performs the system control function 159 to control the ultrasound transmission circuitry 11 and the ultrasound reception circuitry 12, and to transmit ultrasound from the ultrasound probe 70 to a subject P, and to receive a reception signal based on a reflected wave of the ultrasound, which is generated in the subject P. The processing circuitry 15 performs the signal processing function 151 to generate a harmonic signal corresponding to a harmonic component of the reflected wave of the ultrasound generated in the subject P, based on the received reception signal. The processing circuitry 15 performs the calculation function 153 to calculate displacement created in the subject P, using phase information included in the generated harmonic signal, and to calculate a shear wave speed which is an index value indicating tissue properties of the subject P based on the calculated displacement.

Generally, the harmonic component included in the reception signal is less susceptible to multiple reflections than the fundamental wave component, since the main lobe of the harmonic component is thinner than that of the fundamental wave component. For this reason, a calculated shear wave speed may be of a value from which influence of multiple reflections is reduced.

It is thus possible to reduce influence of multiple reflections in elastography.

Noise due to multiple reflections prominently appears in an elasticity image obtained for a subject P who has a thick chest wall. For this reason, with a conventional technique, it is necessary to set a measurement device at a deep location, avoiding the subject's chest wall and its vicinity, where multiple reflections occur. According to the present embodiment, however, it is possible to perform elastography while reducing influence of multiple reflections even at a depth of the chest wall or its vicinity.

In the foregoing embodiment, the processing circuitry 15 performs the image generation function 155 to generate elasticity image data representing an elasticity image based on a harmonic signal of the region of interest, based on a shear wave speed calculated for a harmonic signal calculated for each location in the region of interest of a subject. The processing circuitry 15 performs the display control function 157 to cause the display 50 to display an elasticity image based on the generated harmonic signal, for example the elasticity image 201 shown in FIG. 5. It is thereby possible to display, to an operator, for example, an elasticity image in which noise due to multiple reflections is reduced.

Further according to the foregoing embodiment, the processing circuitry 15 performs the signal processing function 151 and generates a fundamental wave signal corresponding to a fundamental wave component of a reflected wave of ultrasound generated in the subject P based on a received reception signal. The processing circuitry 15 performs the calculation function 153 to calculate displacement created in the subject P, using phase information included in the generated fundamental wave signal, and to calculate a shear wave speed which is an index value indicating tissue properties of the subject P based on the calculated displacement. The processing circuitry 15 performs the image generation function 155, and generates elasticity image data representing an elasticity image based on a harmonic signal of a region of interest based on the shear wave speed calculated for the harmonic calculated for each location in the region of interest in the subject P. The processing circuitry 15 generates elasticity image data representing an elasticity image based on the fundamental wave signal of the region of interest based on shear wave speed calculated for the fundamental wave signal calculated for each location in the region in the subject P. The processing circuitry 15 synthesizes the elasticity image data based on the harmonic signal with the elasticity image based on the fundamental wave signal to generate synthesized elasticity image data.

Generally, a second harmonic component included in a reception signal is more susceptible to attenuation and less sensitive to a distance, compared to a fundamental wave component. According to the present embodiment, the processing circuitry 15 synthesizes a region distant from the ultrasound probe 70 as an elasticity image based on a harmonic signal with a region close to the ultrasound probe 70 as an elasticity image based on a fundamental wave signal. It is thereby possible to correctly illustrate stiffness of living tissue even in a multiplex region. It is thus possible in elastography to secure penetration, while reducing influence of multiple reflections.

(Modification)

In the foregoing embodiment, the processing circuitry 15 performs the PM method, or filtering, to generate a harmonic signal of the reflected wave. As a modification of the embodiment, there may be a case where only filtering is performed to generate a harmonic signal corresponding to a harmonic component.

The configuration of the ultrasound diagnosis apparatus according to this modification is the same as that of the ultrasound diagnosis apparatus 1 shown in FIG. 1.

Figure 7:
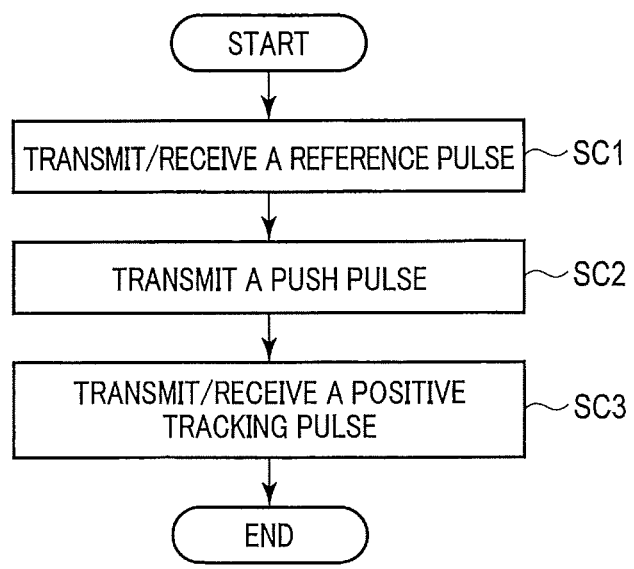
FIG. 7 is a flowchart of ultrasound scanning performed by an ultrasound diagnosis apparatus according to a modification.

Operations of the ultrasound diagnosis apparatus 1 according to the present modification will be described with reference to the drawings. First, the flow of the ultrasound scanning performed by the ultrasound diagnosis apparatus 1, according to the present modification, will be described with reference to FIG. 7. FIG. 7 is a flowchart of the ultrasound scanning performed by the ultrasound diagnosis apparatus 1, according to the present modification. The operations shown in the flowchart are implemented by, for example, the system control function 159. In the following description, let us suppose that a start instruction to start the elastography mode is input via the input interface 20. Further, let us suppose that the processing circuitry 15 generates a harmonic signal of the reflected wave by only using a frequency filter.

Step SC1 and step SC2 shown in FIG. 7 are the same as step SA1 and step SA2 shown in FIG. 2.

After step SC2, the processing circuitry 15 controls the ultrasound transmission circuitry 11, and performs a process of transmitting a tracking pulse at each sample point in a region of interest at least once, in the lateral direction (step SC3). At this time, the processing circuitry 15 transmits only a positive tracking pulse at each sample point in a region of interest at least once. The processing circuitry 15 controls the ultrasound reception circuitry 12, and performs various processes to a reception signal corresponding to the transmitted positive tracking pulse. The processing circuitry 15 may be configured to transmit only a negative tracking pulse at each sample point in a region of interest.

The processing circuitry 15 performs the process in step SC1 through step SC3 in each of the divided regions.

Figure 8:
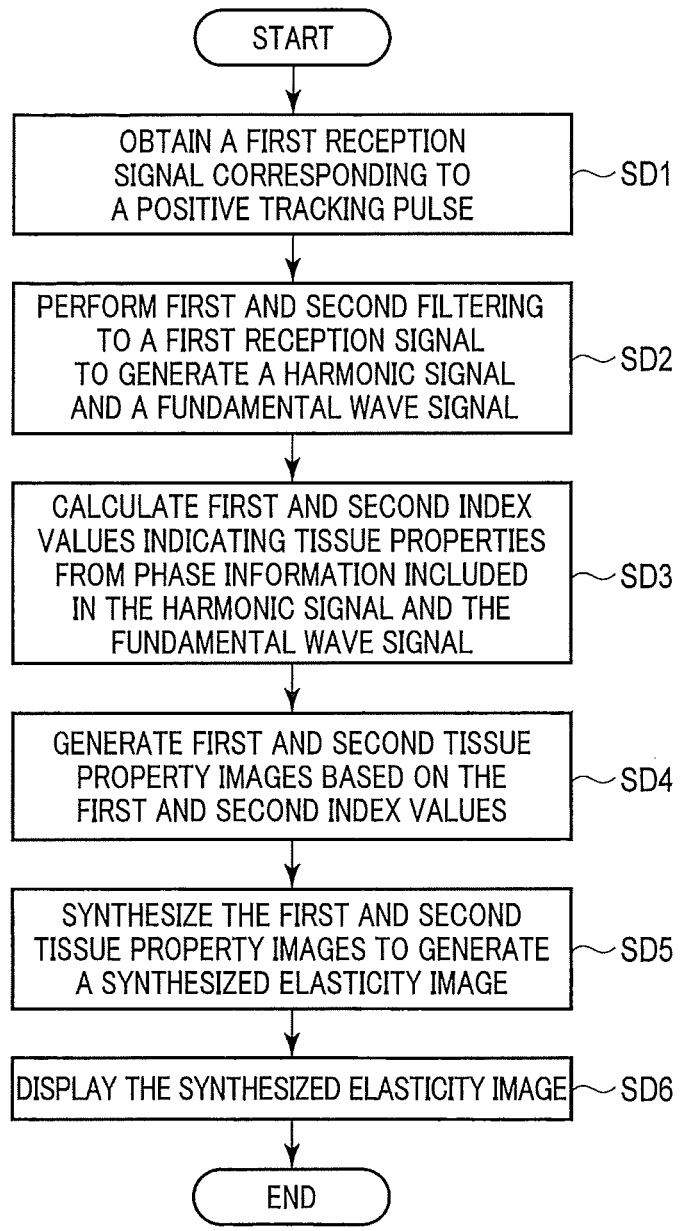
FIG. 8 is a flowchart of operations of processing circuitry when the ultrasound diagnosis apparatus according to the modification displays a synthesized elasticity image.

Next, with reference to FIG. 8, operations of the processing circuitry 15, when the ultrasound diagnosis apparatus 1 according to the present modification displays a synthesized elasticity image, will be described. FIG. 8 is a flowchart of operations of the processing circuitry 15 when the ultrasound diagnosis apparatus 1, according to the modification, displays a synthesized elasticity image. The operations shown in the flowchart are implemented by the signal processing function 151, the calculation function 153, and the image generation function 155. In the following description, let us suppose that the process in step SD1 shown in FIG. 8 is started after the process in step SC1 through step SC3 shown in FIG. 7 is performed in all the divided regions. The process in step SC1 through step SC3 shown in FIG. 7, and the process in step SD1 through step SD4 shown in FIG. 8, may be performed for each divided region. Suppose the harmonic component extracted by the signal processing function 151 is a second harmonic component. The harmonic component extracted by the signal processing function 151 may be a third harmonic component or higher.

The processing circuitry 15 performs the signal processing function 151 to obtain a reception signal of a positive tracking pulse (a first reception signal) for all the divided regions (step SD1). At this time, the processing circuitry 15 obtains the reception signal of a reference pulse generated in step SC1 shown in FIG. 7.

The processing circuitry 15 performs filtering on the first reception signal, using a frequency filter for extracting, for example, only a second harmonic component (a first frequency filter). The processing circuitry 15 performs filtering on the first reception signal, using a frequency filter for extracting, for example, only a fundamental wave component (a second frequency filter). By performing those processes, a harmonic signal corresponding to a second harmonic component and a fundamental wave signal corresponding to the fundamental wave component are generated (step SD2).

In the present embodiment, multiple types of filtering are performed to a tracking pulse; however, a reference pulse may also be subjected to multiple types of filtering.

The process in steps SD4 through SD6 shown in FIG. 8 is the same as the process in steps SB4 through SB7 of FIG. 4.

In this modification, only filtering is performed to generate a harmonic signal corresponding to a harmonic component. For this reason, there is no need for transmission of a tracking pulse multiple times in order to use the PM method, unlike in the foregoing embodiment; accordingly, compared to a case where the PM method is performed, a frame rate of generated elasticity image data can be improved in elastography. Furthermore, it is possible to reduce influence of multiple reflections more easily.

Other Embodiments

In the foregoing embodiment, the ultrasound diagnosis apparatus 1 performs the ultrasound scanning once, which is performed when the PM method is used, in order to generate a harmonic signal and a fundamental wave signal; however, the ultrasound scanning may be performed in a different manner. For example, the ultrasound diagnosis apparatus 1 may perform ultrasound scanning, which is performed when the PM method is used, in order to generate a harmonic component, and may separately perform ultrasound scanning, which is performed in normal elastography, in order to generate a fundamental wave signal.

In the foregoing embodiment, the ultrasound diagnosis apparatus 1 performs elastography by applying acoustic radiation force as a push pulse to living tissue in order to cause displacement; however, the embodiment is not limited thereto. The ultrasound diagnosis apparatus 1 may perform elastography by applying mechanical vibration generated by an external device to living tissue so as to cause displacement in the living tissue, for example. At this time, in the foregoing embodiment, when performing ultrasound scanning, a process of transmitting a push pulse, for example step SA2 in FIG. 2 and step SC2 in FIG. 7, may be omitted.

In the foregoing embodiment, the ultrasound diagnosis apparatus 1 calculates a propagation speed of a shear wave generated by a push pulse to measure stiffness of living tissue and to generate elasticity image data; however, the embodiment is not limited thereto. For example, the ultrasound diagnosis apparatus 1 may generate elasticity image data by measuring stiffness of living tissue based on strain caused by applying a pressure to a subject P using the ultrasound probe 70.

In the foregoing embodiment, the ultrasound diagnosis apparatus 1 performs elastography to measure stiffness of living tissue; however, the embodiment is not limited thereto. The ultrasound diagnosis apparatus 1 performs elastography to evaluate viscosity of living tissue based on a relationship between a frequency and a propagation speed of a shear wave. An index value indicating viscosity of living tissue is utilized in diagnosis of cases where a great increase of viscosity is observed due to necrosis or inflammation, such as acute hepatitis.

In the foregoing embodiment, the processing circuitry 15 may be configured to display an index value indicating tissue properties, along with a synthesized elasticity image. In this case, the processing circuitry 15 calculates a plurality of index values related to tissue properties based on displacement caused in a subject. The processing circuitry 15 calculates a modulus of elasticity and a viscosity coefficient, etc. based on, for example, a shear wave speed at each sample point used for generating synthesized elasticity image data. The processing circuitry 15 generates an image indicating at least two or more index values, among the calculated index values. The image is displayed in the form of diagram as diagnosis support information that expresses, for example, qualitative data relating to a region of interest. The processing circuitry 15 causes the display 50 to display an image indicating the generated index values, side by side with a synthesized elasticity image, or superimposing the image and the synthesized elasticity image.

In the foregoing embodiment, the processing circuitry 15 may cause the display 50 to display a difference image simultaneously with a plurality of line images. A line image is an image drawn by lines each representing an identical arrival time of a shear wave at, for example, each point (each location) in a region of interest (which may be referred to as a contour image). At this time, the processing circuitry 15 generates line image data representing the plurality of line images. The line image data consists of information for displaying contour lines which each connect locations where a shear wave arrives at approximately the identical time. For example, the processing circuitry 15 extracts multiple points having an identical predetermined arrival time among the points ("sample points") in the region of interest. The processing circuitry 15 then generates line image data by connecting the extracted multiple points. The processing circuitry 15 performs a process of generating such line image data for multiple phases. The predetermined arrival time is a value designated in advance by an operator or a designer of the ultrasound diagnosis apparatus 1, and a plurality of values are usually designated. The processing circuitry 15 displays the difference image and the plurality of line images image side by side, or by superimposition. It is thus possible for an operator to look at an elasticity image while checking how a shear wave propagates, or if a shear wave is generated and propagates as expected.

Figure 9:
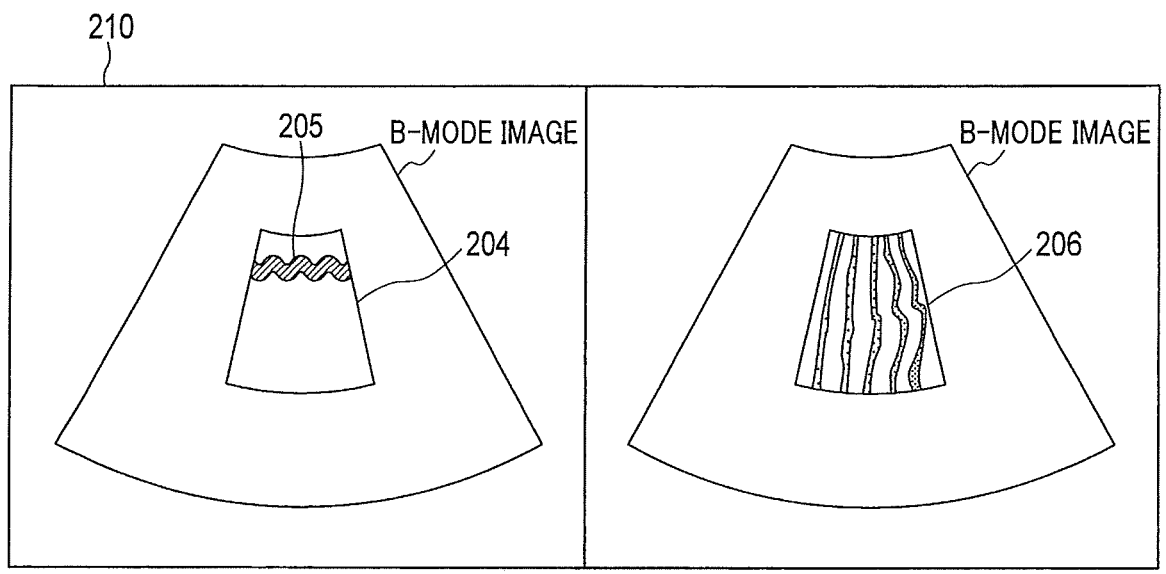
FIG. 9 is a diagram illustrating an example where a difference image and a contour image are displayed side by side in an ultrasound diagnosis apparatus according to another embodiment.

FIG. 9 is a diagram illustrating an example where a difference image and a contour image are displayed side by side in the ultrasound diagnosis apparatus according to another embodiment. FIG. 9 illustrates the display region 210 of the display 50. Two B-mode images are displayed side by side in the display region 210. On one of the B-mode images (located on the left in the display region 210), a difference image 204 including the region 205 illustrated by shading is superimposed. On the other B-mode image (the right in the display region 210), a contour image 206 is superimposed.

Figure 10:
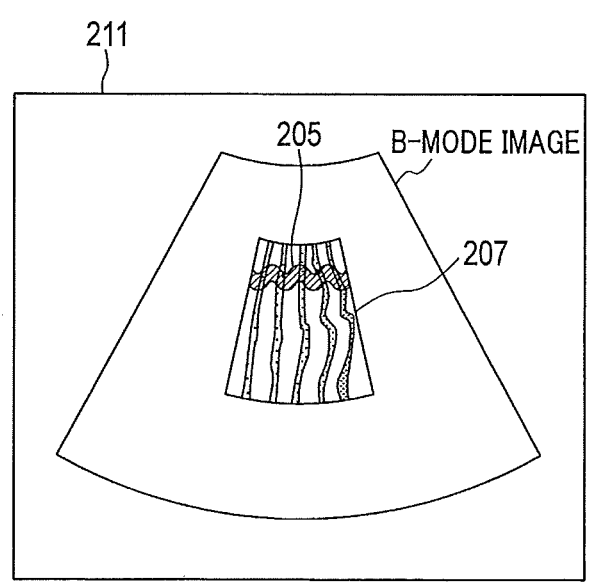
FIG. 10 is a diagram illustrating an example where a difference image and a contour image are superimposed and displayed in the ultrasound diagnosis apparatus according to the another embodiment.

FIG. 10 is a diagram illustrating an example where a difference image and a contour image are superimposed and displayed in the ultrasound diagnosis apparatus according to the another embodiment. FIG. 10 illustrates the display region 211 of the display 50. A B-mode image is displayed in the display region 210. On this B-mode image, the region 205 illustrated by shading and a contour image 207 are superimposed.

In the foregoing embodiment, the processing circuitry 15 may perform synthesis of the elasticity image based on the harmonic signal and the elasticity image based on the fundamental wave signal throughout the image. The processing circuitry 15 may perform the synthesis of the elasticity image based on the harmonic signal and the elasticity image based on the fundamental wave signal, only to the elasticity image based on the harmonic signal, or only to a specific region in the elasticity image based on the fundamental wave signal.

In the foregoing embodiment, the ultrasound diagnosis apparatus 1 performs the transmission of a push pulse and the transmission and reception of a tracking pulse from one ultrasound probe 70; however, the embodiment is not limited thereto. The ultrasound diagnosis apparatus 1 may have a plurality of ultrasound probes, and an ultrasound probe that transmits a push pulse may be different from the one that transmits/receives a tracking pulse.

In the foregoing embodiment, the ultrasound diagnosis apparatus 1 generates a first tissue property image and a second tissue property image, and generates one tissue property image (a third tissue property image) by synthesizing or superimposing these two tissue property images; however, the embodiment is not limited thereto. The ultrasound diagnosis apparatus 1 may generate one tissue property image by performing two types of filtering to a reception signal in accordance with a location in the region of interest, in other words, by filtering a reception signal with a frequency filter in accordance with a depth, without generating two tissue property images.

In this case, the processing circuitry 15 generates, by the signal processing function 151, an analysis signal by filtering a reception signal received from the ultrasound reception circuitry 12 with a frequency filter in accordance with a depth. The analysis signal includes a harmonic signal corresponding to a harmonic component and a fundamental wave signal corresponding to a fundamental wave component, for example. The processing circuitry 15 calculates, by the calculation function 153, index values indicating tissue properties of a subject based on the generated analysis signal. The processing circuitry 15 displays, by the display control function 157, an analysis result based on the calculated index values.

The processing circuitry 15 may further generate, by the image generation function 155, a tissue property image corresponding to the region of interest as the analysis result. The processing circuitry 15 may calculate, via the calculation function 153, displacement generated in a subject by using phase information of a generated analysis signal, and may calculate the index values based on the calculated displacement.

Furthermore, the processing circuitry 15 may generate, via the image generation function 155, a contour image illustrating the lines representing approximately the same arrival times when a shear wave arrives at each location in the region of interest, and may display, by the display control function 157, the tissue property image and the generated contour image simultaneously, while also displaying the analysis result.

Figure 11:
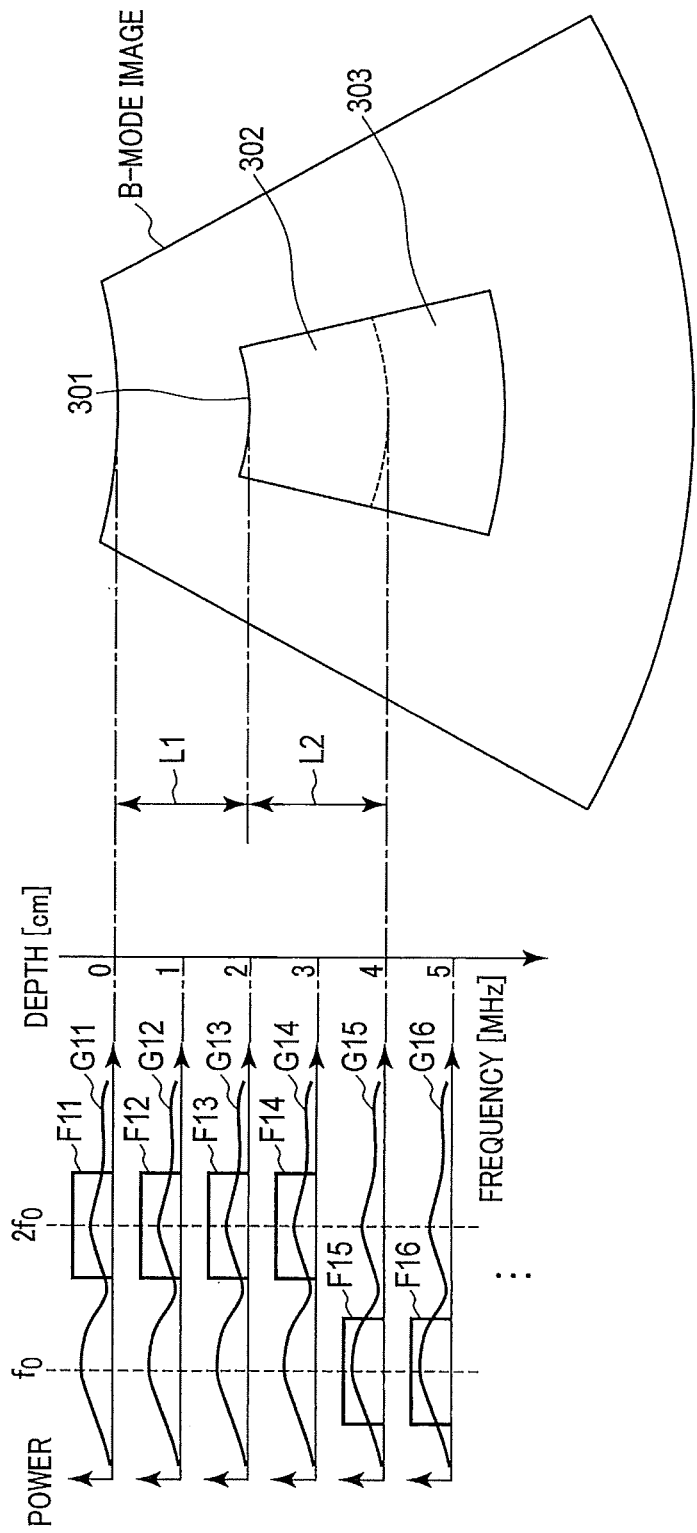
FIG. 11 is a diagram illustrating a process of displaying a synthesized elasticity image by the ultrasound diagnosis apparatus according to the another embodiment.

FIG. 11 is a diagram illustrating a process of displaying a synthesized elasticity image via the ultrasound diagnosis apparatus according to the another embodiment. FIG. 11 shows a B-mode image, associated with frequency filters that are respectively set in accordance with a distance (a depth) measured from the body surface. The depth shown in FIG. 11 is a depth from the body surface and corresponds to a depth of a scanning cross section displayed in the B-mode image, for example. Let us suppose that the scanning cross section is a cross section obtained when an abdomen is scanned.

In the following, let us suppose that each location in the region of interest corresponds to a depth in the scanning cross section of the abdomen. The length L1 represents the range of the area of an abdominal wall, and the length L2 represents the range of the area that can be affected by multiple reflections caused by an abdomen wall. The length L1 is set by image analysis performed to B-mode image, etc., or by an operator's input, for example. Alternatively, L1 (or L2) may be set based on patient information by referring to a table showing the relationship between the patient information (for example, information regarding body figure, such as percent of body fat or BMI index) and L1 (or L2). Herein, since the range of an abdominal wall and the range of the area affected by multiple reflections have approximately the same depth, the length L1 and the length L2 are approximately the same value. In other words, if the length L1 is set, the length L2 is determined. Accordingly, the processing circuitry 15 sets a first frequency filter only for extracting a secondary harmonic component in the range of a length (depth) obtained by adding the length L1 and the length L2 (hereinafter, a "multiple reflection region"), and sets a second frequency filter only for extracting a fundamental wave component in other range (hereinafter, a "deep portion region").

The synthesized elasticity image 301 on a B-mode image shows two regions, a first region 302 and a second region 303. The synthesized elasticity image 301 is equivalent to a tissue property image. The region shown in the synthesized elasticity image 301 is equivalent to an imaging ROI. The first region 302 is included in, for example, the multiple reflection region, and the second region 303 is included in the deep portion region.

The processing circuitry 15 sets, by the signal processing function 151, a frequency filter corresponding to a depth of the scanning. As an example, the processing circuitry 15 sets a first frequency filter of the central frequency $2f_0$ to the depth of 0 cm to 4 cm, which is a sum of the length L1 and the length L2, and sets a second frequency filter of the central frequency $f_0$ to the depth of 4 cm or deeper.

For example, in the depth of 0 cm to 1 cm, if a reception signal indicating a receive frequency characteristic graph G11 is obtained, the central frequency of the frequency filter F11 is $2f_0$. In the depth of 1 cm to 2 cm, if a reception signal indicating a receive frequency characteristic graph G12 is obtained, the central frequency of the frequency filter F12 is $2f_0$. In the depth of 2 cm to 3 cm, if a reception signal indicating a reception frequency characteristic graph G13 is obtained, a central frequency of the frequency filter F13 is $2f_0$. In the depth of 3 cm to 4 cm, if a reception signal indicating a reception frequency characteristic graph G14 is obtained, a central frequency of the frequency filter F14 is $2f_0$. Thus, the frequency filters F11 through F14 are a first frequency filter.

For example, in the depth of 4 cm to 5 cm, if a reception signal indicating a receive frequency characteristic graph G15 is obtained, a central frequency of the frequency filter F15 is $f_0$. In the depth of 5 cm or deeper, if a reception signal indicating a receive frequency characteristic graph G16 is obtained, a central frequency of the frequency filter F16 is $f_0$. Thus, the frequency filters F15 and F16 are a second frequency filter.

In summary, the processing circuitry 15 sets a first frequency filter or a second frequency filter for each location in the region of interest in accordance with a relative positional relationship between the abdominal wall and the region of interest. Since the first region 302 is included in the multiple reflection region, the processing circuitry 15 uses the first frequency filter. Since the second region 303 is included in the deep portion region, the processing circuitry 15 uses the second frequency filter.

Figure 12:
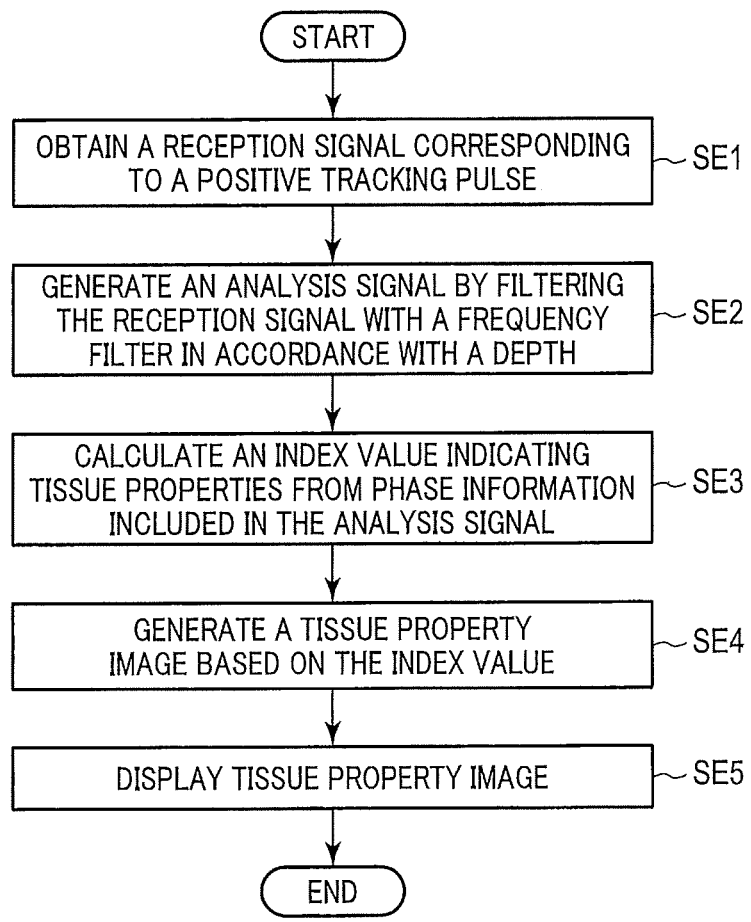
FIG. 12 is a flowchart of operations of processing circuitry when the ultrasound diagnosis apparatus according to the another embodiment displays a synthesized elasticity image.

FIG. 12 is a flowchart of operations of processing circuitry when the ultrasound diagnosis apparatus, according to the another embodiment displays a synthesized elasticity image. The operations shown in the flowchart are implemented by the signal processing function 151, the calculation function 153, the image generation function 155, and the display control function 157. In the following description, suppose the process in step SE1 shown in FIG. 12 is started after the process in step SC1 through step SC3 shown in FIG. 7 is performed in the region of interest. Suppose the harmonic component extracted by the signal processing function 151 is a second harmonic component. The harmonic component extracted by the signal processing function 151 may be a third harmonic component or higher.

(Step SE1)

The processing circuitry 15 obtains a reception signal corresponding to a positive tracking pulse for a region of interest. At this time, the processing circuitry 15 obtains the reception signal of a reference pulse generated in step SC1 shown in FIG. 7.

(Step SE2)

By performing the signal processing function 151, the processing circuitry 15 performs filtering to the reception signal with a frequency filter in accordance with a depth, and generates an analysis signal. Specifically, the processing circuitry 15 sets a first frequency filter or a second frequency filter for each location in the region of interest, in accordance with a relative positional relationship between the abdominal wall and the region of interest. The processing circuitry 15 performs first frequency filtering to a reception signal corresponding to a first region in the region of interest, and second frequency filtering to a reception signal corresponding to a second region in the region of interest. The reception signal of a reference pulse may be filtered in a similar manner.

(Step SE3)

The processing circuitry 15 performs the calculation function 153 to calculate an index value indicating tissue properties from phase information included in the analysis signal.

(Step SE4)

The processing circuitry 15 performs the image generation function 155 to generate a tissue property image based on the index value.

(Step SE5)

The processing circuitry 15 performs the display control function 157 and causes the display 50 to display the tissue property image.

As described above, the ultrasound diagnosis apparatus 1 generates the tissue property image by performing two types of filtering to a reception signal in accordance with a location in the region interest, without generating first and second tissue property images.

If numerical information (e.g., a stiffness value) is displayed as an analysis result, in step SE2, the processing circuitry 15 performs the signal processing function 151 and sets a frequency filter (a first frequency filter or a second frequency filter) corresponding to a desired location in the region of interest. The processing circuitry 15 performs the frequency filtering to a reception signal corresponding to the desired location in the region of interest, and generates an analysis signal. In step SE3, the processing circuitry 15 performs the calculation function 153 to calculate a stiffness by using an analysis signal. In step SE5, the processing circuitry 15 performs the display control function 157 to display the stiffness value on the display 50. The process in step SE4 is omitted in this case.

If the entire region of interest is included in the multiplex reflection region, index value may be calculated by using a first frequency filter only, and if the entire region of interest is included in the depth region, index value may be calculated by using a second frequency filter only. In other words, a frequency filter may be selected in accordance with a size and a location of the region of interest.

In the foregoing embodiment, the ultrasound diagnosis apparatus 1 performs two types of filtering to a reception signal in accordance with a location in the region of interest so as to generate a third tissue property image; however, the embodiment is not limited thereto. The ultrasound diagnosis apparatus 1 may generate a third tissue property image by performing three or more types of filtering to a reception signal in accordance with a location in the region interest.

In this case, the processing circuitry 15 generates, via the signal processing function 151, an analysis signal at each location in the region of interest based on the location, and a reception signal received from the ultrasound reception circuitry 12. The analysis signal includes a harmonic signal corresponding to a harmonic component and a fundamental wave signal corresponding to a fundamental wave component, for example. The analysis signal may include a difference tone signal, corresponding to a difference tone component, based on a difference tone generated by a non-linear effect. The analysis signal may include a signal corresponding to a component included in a bandwidth of a receive central frequency selected as appropriate (for example, a tone component). Each of a harmonic component, a difference tone component, and a tone component may be called non-linear component for how they are produced.

FIG. 13 is a diagram illustrating a process of displaying a synthesized elasticity image by the ultrasound diagnosis apparatus according to the another embodiment. FIG. 13 shows a B-mode image, associated with frequency filters, similar to FIG. 11. In the description of FIG. 13, suppose the ultrasound diagnosis apparatus transmits a pulse at a central frequency $f_1$ and a pulse at a central frequency $f_2$ simultaneously, and uses a difference tone component and a harmonic component respectively corresponding to a central $(f_2-f_1)$ and a central frequency $2f_1$.

The synthesized elasticity image 311 on a B-mode image shows four regions, a first region 312, a second region 313, a third region 314, and a fourth region 315. The synthesized elasticity image 311 is equivalent to a tissue property image. The region shown in the synthesized elasticity image 311 is equivalent to a region of interest. The first region 312 and the second region 313 are included in, for example, the multiple reflection region, and the third region 314 and the fourth region 315 are included in the deep portion region.

The processing circuitry 15 sets a frequency filter in accordance with a depth of a scanning cross section, by the signal processing function 151. As an example, the processing circuitry 15 sets a frequency filter of the central frequency $2f_1$ for the depth of 0 cm to 3 cm, and sets a filter of a central frequency between $(f_2-f_1)$ and $2f_1$ for the depth of 3 cm to 4 cm. The processing circuitry 15 sets a frequency filter of the central frequency $f_2-f_1$ for the depth of 4 cm to 5 cm, and sets a frequency filter of the central frequency $f_1$ for the depth of 5 cm or deeper.

For example, in the depth of 0 cm to 1 cm, if a reception signal indicating a receive frequency characteristic graph G21 is obtained, a central frequency of the frequency filter F21 is $2f_1$. In the depth of 1 cm to 2 cm, if a reception signal indicating a receive frequency characteristic graph G22 is obtained, a central frequency of the frequency filter F22 is $2f_1$. In the depth of 2 cm to 3 cm, if a reception signal indicating a receive frequency characteristic graph G23 is obtained, a central frequency of the frequency filter F23 is $2f_1$.

In the depth of 3 cm to 4 cm, if a reception signal indicating a receive frequency characteristic graph G24 is obtained, a central frequency of the frequency filter F24 is between $(f_2-f_1)$ and $2f_1$. In the depth of 4 cm to 5 cm, if a reception signal indicating a receive frequency characteristic graph G25 is obtained, a central frequency of the frequency filter F25 is $f_2-f_1$. In the depth of 5 cm or deeper, if a reception signal indicating a receive frequency characteristic graph G26 is obtained, a central frequency of the frequency filter F26 is $f_1$.

In summary, the processing circuitry 15 sets a frequency filter for each location in the region of interest, in accordance with a relative position relationship between the abdominal wall and the region of interest. If a signal having a central frequency of $(f_2-f_1)$, which is a difference tone component, is generated, the processing circuitry 15 can set a frequency filter having a central frequency within the range of a fundamental wave frequency, in turn having the central frequency of $f_1$, to a harmonic frequency having the central frequency of $2f_1$. Depending on a combination of frequency components included in the transmit wave, multiple non-linear components overlap in the same frequency bandwidth; in such a case, it is possible to extract more than one non-linear component with one filter.

(Another Modification)

In each of the foregoing embodiments, a synthesized elasticity image is generated by the ultrasound diagnosis apparatus 1. In this another modification, a synthesized elasticity image is generated by an analysis apparatus having at least the functions implemented in the processing circuitry 15 of the ultrasound diagnosis apparatus 1.

The analysis apparatus according to this another modification has, for example, processing circuitry 15, internal storage circuitry 17, an input interface 20, a display 50, and an input device 60, which are shown in FIG. 1. The analysis apparatus is connected directly or via a network 100 to, for example, an ultrasound diagnosis apparatus.

In the present modification, the processing circuitry 15 is a processor that functions as a main unit of the analysis apparatus. The processing circuitry 15 performs an operation program stored in the internal storage circuitry 17 to realize a function corresponding to the operation program. Specifically, the processing circuitry 15 includes a signal processing function 151 (signal processor), a calculation function 153 (calculator), an image generation function 155 (image generator), a display control function 157 (display controller), and a system control function 159.

The signal processing function 151 is a function to perform various kinds of signal processing on the reception signal generated by the ultrasound diagnosis apparatus.

Specifically, the processing circuitry 15 performs the signal processing function 151 to generate a harmonic signal based on a reception signal that is collected by an ultrasound probe and to generate a fundamental wave signal based on the reception signal. The ultrasound probe transmits ultrasound to a subject, receives a reflected wave of the ultrasound generated in the subject, and generates the reception signal based on the reflected wave. The harmonic signal corresponds to a harmonic component of the reflected wave. The fundamental wave signal corresponds to a fundamental wave component of the reflected wave.

Alternatively, the processing circuitry 15 performs the signal processing function 151 to generate an analysis signal at a location in a region of interest based on the location and a reception signal that is collected by an ultrasound probe. The ultrasound probe transmits ultrasound to a subject, receives a reflected wave of the ultrasound generated in the subject, and generates the reception signal based on the reflected wave.

The system control function 159 is a function of controlling an input and an output of the analysis apparatus. The processing circuitry 15 receives, by the system control function 159, a start instruction in order to start the processing of generating a synthesized elasticity image via the input interface 20.

Since the calculation function 153, the image generation function 155, the display control function 157, and the system control function 159 are approximately the same as the aforementioned, the descriptions thereof are omitted.

The term "processor" used in the above description means, for example, a central processing unit (CPU), a graphics processing unit (GPU), or circuitry such as an application specific integrated circuit (ASIC), a programmable logic device (e.g., a simple programmable logic device (SPLD), a complex programmable logic device (CPLD), or a field programmable gate array (FPGA). The processor realizes its function by reading and executing the program stored in the storage circuitry. Each processor of the present embodiment is not limited to a case where each processor is configured as a single circuit; a plurality of independent circuits may be combined into a single processor to realize the function of the processor. In addition, a plurality of structural elements in FIG. 1 may be integrated into a single processor to realize the function.

According to at least one of the above-described embodiments, it is possible to improve the quality of quantification of tissue properties.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An analysis apparatus, comprising:
processing circuitry configured to:
  generate a harmonic signal based on a reception signal that is collected by an ultrasound probe, and generate a fundamental wave signal based on the reception signal, the ultrasound probe transmitting ultrasound to a subject, receiving a reflected wave of the ultrasound generated in the subject, and generating the reception signal based on the reflected wave, the harmonic signal corresponding to a harmonic component of the reflected wave, the fundamental wave signal corresponding to a fundamental wave component of the reflected wave,
  calculate a first index value indicating tissue properties of the subject based on the harmonic signal, and calculate a second index value indicating the tissue properties based on the fundamental wave signal;
  generate an analysis result based on the first index value and the second index value;
  display the analysis result;
wherein
the processing circuitry is further configured to:
  generate a first tissue property image corresponding to a first region in a region of interest based on the first index value;
  generate a second tissue property image corresponding to a second region in the region of interest based on the second index value, the second region being different from the first region;
  generate a third tissue property image corresponding to the region of interest as the analysis result by synthesizing the first tissue property image and the second tissue property image
  calculate a first displacement caused in the subject by using phase information of the harmonic signal;
  calculate the first index value based on the first displacement;
  calculate a second displacement caused in the subject by using phase information of the fundamental wave signal; and
  calculate the second index value based on the second displacement.

2. The analysis apparatus according to claim 1, wherein the display of the analysis result is a display of the third tissue property image which is obtained by superimposing the first tissue property image and the second tissue property image.

3. The analysis apparatus according to claim 1, wherein the processing circuitry is further configured to:
  generate the harmonic signal by using a first frequency filter for the harmonic component; and
  generate the harmonic signal by using a second frequency filter for the fundamental wave component.

4. The analysis apparatus according to claim 3, wherein the first frequency filter passes a central frequency in accordance with a depth where the reflected wave is generated.

5. The analysis apparatus according to claim 1, wherein the ultrasound probe transmits first ultrasound and generates a first reception signal based on a first reflected wave corresponding to the first ultrasound,
the ultrasound probe transmits second ultrasound which has an inversion of the phase of the first ultrasound and generates a second reception signal based on a second reflected wave corresponding to the second ultrasound, and
the processing circuitry is further configured to generate the harmonic signal and the fundamental wave signal using the first reception signal and the second reception signal.

6. The analysis apparatus according to claim 1, wherein the processing circuitry is further configured to generate a difference image by taking a difference between the first tissue property image and the second tissue property image.

7. The analysis apparatus according to claim 6, wherein the display of the analysis result is a simultaneous display of the third tissue property image and the difference image.

8. The analysis apparatus according to claim 1, wherein the processing circuitry is further configured to generate a contour image showing a line representing an identical arrival time of a shear wave at each location in the region of interest.

9. The analysis apparatus according to claim 8, wherein the display of the analysis result is a simultaneous display of the third tissue property image and the contour image.

10. The analysis apparatus according to claim 6, wherein the processing circuitry is further configured to generate a contour image showing a line representing an identical arrival time of a shear wave at each location in the region of interest, and
the display of the analysis result is a simultaneous display of the contour image and the difference image.

11. An analysis method, comprising:
generating a harmonic signal based on a reception signal that is collected by an ultrasound probe, and generating a fundamental wave signal based on the reception signal, the ultrasound probe transmitting ultrasound to a subject, receiving a reflected wave of the ultrasound generated in the subject, and generating the reception signal based on the reflected wave, the harmonic signal corresponding to a harmonic component of the reflected wave, the fundamental wave signal corresponding to a fundamental wave component of the reflected wave,
calculating a first index value indicating tissue properties of the subject based on the harmonic signal, and calculating a second index value indicating the tissue properties based on the fundamental wave signal; and
displaying an analysis result based on the first index value and the second index value;
wherein the analysis method further includes,
  generating a first tissue property image corresponding to a first region in a region of interest based on the first index value, including, calculating a first displacement caused in the subject by using phase information of the harmonic signal, and calculating the first index value based on the first displacement;

generating a second tissue property image corresponding to a second region in the region of interest based on the second index value, the second region being different from the first region, including, calculating a second displacement caused in the subject by using phase information of the fundamental wave signal, and calculating the second index value based on the second displacement;

generating a third tissue property image corresponding to the region of interest as the analysis result by synthesizing the first tissue property image and the second tissue property image.

\* \* \* \* \*